United States Patent
Hopper

(10) Patent No.: US 6,221,630 B1
(45) Date of Patent: Apr. 24, 2001

(54) HIGH COPY NUMBER RECOMBINANT EXPRESSION CONSTRUCT FOR REGULATED HIGH-LEVEL PRODUCTION OF POLYPEPTIDES IN YEAST

(75) Inventor: James E. Hopper, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/275,680

(22) Filed: Mar. 24, 1999

(51) Int. Cl.⁷ .............................. C12P 21/02; C12N 15/81

(52) U.S. Cl. ................ 435/69.1; 435/254.2; 435/254.21; 435/254.23; 435/320.1; 435/483

(58) Field of Search ................................. 435/69.1, 254.2, 435/254.21, 254.23, 320.1, 455, 483; 530/350

(56) References Cited

PUBLICATIONS

Romanos et al. (1992) Foreigh gene expression in yeast: a review. Yeast 8:423–488, 1992.*
Broach et al., 1979, Gene 8:121–133.
Rose and Broach, 1990, Methods Enzymol. 185:234–279.
Broach and Hicks, 1980, Cell 2:501–508.
Bolivar et al., 1977, Gene 2: 95–113.
Irani et al. 1987, Mo. Cell Biol. 7:1233–1241.
Reece and Platt, 1997, Bioessays 19:1001–1010.
Koh et al., 1988, Molecular Cell 1:895–904.
Wu et al., 1996, Embo J. 15:3951–3963.
Torchia and Hopper, 1986, Genetics 113: 229–246.
Lue et al., Mol. Cell Bio. 7:3446–3451, 1987.
Suzuki–Fujimoto et al., 1996, Mol. Cell. Biol. 16:2504–2508.
Johnston and Hopper, 1982, Proc. Natl. Acad. Sci. USA 79:6971–6975.
Nogi et al., 1984, Mol. Gen. Genet. 195: 29–34.
Bhat and Hopper, 1992, Mol. Cell. Biol. 12:2701–2707.
Laughon and Gesteland, 1982, Proc. Nat'l. Acad. Sci. USA 79:6827–6831.
Laughon et al., 1984, Molec. Cell Biol. 4:268.
Gill & Ptashne, 1988, Nature 334:721–724.
Mylin et al., 1990, in Methods in Enzymology, Colowick and Kaplan, eds., vol. 185, pp. 297–308.
Martegani et al., 1993, Yeast 9:575–582.
Mylin & Hopper, 1996 in Methods in Molecular Biology, Tuan, ed., vol. 62.
Hirst et al., 1994, Embo J. 13:5410–5420.
Kwast et al., 1998, J. Exp. Biol 201:1177–1195.
Zhang & Guarante, 1995, Embo J 14:313–320.
Pfeifer et al, 1989, Cell 56:291–301.
Lesage et al., 1996, Molec. Cell Biol. 16:1921–1928.
Treitel & Carlson, 1995, Proc. Natl. Acid. Sci. USA 92:3132–3136.
Broach, 1983, Methods Enzymol. 101:307–325.
Kang et al., 1993, J. Biol. Chem. 268:9629–9635.
Bram & Kornberg, 1985, Proc. Natl. Acad. Sci. USA 82:43–47.
Giniger et al., 1985, Cell 40:767–774.
Carey et al., 1989, J. Molec. Biol. 209:423–432.
Tajima et al., 1986, Molec. Cell Biol. 6:246–256.
Summer–Smith et al., 1985, Gene 36:33–340.
Bram et al., 1986 Embo J. 5:603–608.
Nogi et al., 1984, Nucl Acids Res. 12:9287–9298.
Bajwa et al., 1988, Molec. Cell. Biol 8:3439–3447.
Szkutnicka et al., 1989, J. Bacteriol 171:4486–4493.
Angermayr et al., 1997, Molec. Biol. 186:821–824.
Cregg et al., 1985, Mol. Cell Biol. 5:3376–3385.
Raymond et al., 1998 Yeast 14:11–23.
Sears et al., 1988, Yeast 14:11–23.
Sreekrishna et al., 1984, Gene 28:73–81.
Riley et al., 1987, Mol Cell Biol 7:780–786.
Schulz et al., 1993, Biol. Chem 374:313–318.
Webster and Dickson, 1988 Nucleic Acids Res. 16:8192–8193.
Webster and Dickson, 1988, Nucleic Acids Res. 16:8011–8027.
Adamikova 1998, et al., Yeast, 14:805–812.
Bogdanova et al., 1998, Yeast 14:1–9.
Davidow et al., 1985, Curr. Genet. 10:39–48.
Farrar and Williams, 1988, Trends Genet. 4:343–348.
Gleeson et al., 1986, J. Gen. Microbiol. 132:3459–3465.
Klein and Favreau, 1998, J. Bacteriol 170:5572–5578.
Roggenkamp et al., 1986, Mol. Gene Genet 202:302–308.
Tikhomirova et al., 1986, Curr. Genet. 10:741–747.
Matsumoto et al., 1978, J. Bacteriol. 134:446–457.
Lemire et al., 1985, Mol. Cell. Biol. 5:2131–2141.

(List continued on next page.)

*Primary Examiner*—Robert A. Schwartzman
(74) *Attorney, Agent, or Firm*—Thomas J. Monahan

(57) ABSTRACT

The invention provides methods and recombinant expression constructs for inducing and sustaining high-level production of a recombinant polypeptide in yeast. The invention specifically provides high copy number recombinant expression constructs that express high levels of trans-acting transcription factors that in turn induce expression of a recombinant nucleic acid encoding a heterologous or endogenous recombinant polypeptide. The invention more specifically provides constructs that express galactose-inducible and temperature-sensitive transcription factors. The invention also provides constructs comprising nucleic acids the transcription of which is regulated by the transcription factors expressed by the construct. The invention also provides yeast cells transformed by the recombinant expression constructs of the invention that permit sustained high-level expression of a recombinant polypeptide. The invention further provides methods for producing yeast cells transformed with the recombinant expression constructs of the invention, and methods for inducing high-level expression of a recombinant polypeptide in said transformed yeast cells. The invention also provides such recombinant polypeptides produced by the methods and the transformed yeast cells of the invention.

53 Claims, 2 Drawing Sheets

OTHER PUBLICATIONS

Hsu & Kohlhaw, 1982, J. Biol. Chem 257:39–41.
Sikorski and Hieter, 1989, Genetics 122:19–27.
Post–Beittenmiller et al., 1984, Molec. Cell Biol. 4:1238–1245.
Kolodziej and Young, 1991, Methods in Enzymology 194:508–519.
Field et al., 1988, Molec. Cell Biol 8:2159–2165.
Cavender et al., 1995, J. Virol 69:923–934.

* cited by examiner

SEQUENCE LISTING

<160> NUMBER OF SEQ ID NOS: 22

<210> SEQ ID NO 1
<211> LENGTH: 17
<212> TYPE: DNA
<213> ORGANISM: Saccharomyces cerevisiae

<400> SEQUENCE: 1
cggaggactg tcctccg        17

<210> SEQ ID NO 2
<211> LENGTH: 17
<212> TYPE: DNA
<213> ORGANISM: Saccharomyces cerevisiae

<400> SEQUENCE: 2
cggattagaa gccgccg        17

<210> SEQ ID NO 3
<211> LENGTH: 17
<212> TYPE: DNA
<213> ORGANISM: Saccharomyces cerevisiae

<400> SEQUENCE: 3
cgggtgacag ccctccg        17

<210> SEQ ID NO 4
<211> LENGTH: 17
<212> TYPE: DNA
<213> ORGANISM: Saccharomyces cerevisiae

<400> SEQUENCE: 4
aggaagactc tcctccg        17

<210> SEQ ID NO 5
<211> LENGTH: 17
<212> TYPE: DNA
<213> ORGANISM: Saccharomyces cerevisiae

```
<400> SEQUENCE: 5
cgcgccgcac tgctccg                                                    17

<210> SEQ ID NO 6
<211> LENGTH: 17
<212> TYPE: DNA
<213> ORGANISM: Saccharomyces cerevisiae

<400> SEQUENCE: 6
cggacaactg ttgaccg                                                    17

<210> SEQ ID NO 7
<211> LENGTH: 17
<212> TYPE: DNA
<213> ORGANISM: Saccharomyces cerevisiae

<400> SEQUENCE: 7
gcctgttgac aactggc                                                    17

<210> SEQ ID NO 8
<211> LENGTH: 17
<212> TYPE: DNA
<213> ORGANISM: Saccharomyces cerevisiae

<400> SEQUENCE: 8
cggccatatg tcttccg                                                    17

<210> SEQ ID NO 9
<211> LENGTH: 17
<212> TYPE: DNA
<213> ORGANISM: Saccharomyces cerevisiae

<400> SEQUENCE: 9
cggcgcactc tcgcccg                                                    17

<210> SEQ ID NO 10
<211> LENGTH: 15
<212> TYPE: DNA
<213> ORGANISM: Saccharomyces cerevisiae

<400> SEQUENCE: 10
cgctacaatg acccg                                                      15

<210> SEQ ID NO 11
<211> LENGTH: 17
<212> TYPE: DNA
<213> ORGANISM: Saccharomyces cerevisiae

<400> SEQUENCE: 11
cggtccactg tgtgccg                                                    17

<210> SEQ ID NO 12
<211> LENGTH: 23
<212> TYPE: DNA
<213> ORGANISM: Saccharomyces cerevisiae

<400> SEQUENCE: 12
tatcggggcg gatcactccg aac                                             23

<210> SEQ ID NO 13
<211> LENGTH: 23
<212> TYPE: DNA
<213> ORGANISM: Saccharomyces cerevisiae
```

```
<400> SEQUENCE: 13
caccggcggt ctttcgtccg tgc                                          23

<210> SEQ ID NO 14
<211> LENGTH: 15
<212> TYPE: DNA
<213> ORGANISM: Saccharomyces cerevisiae

<400> SEQUENCE: 14
ggagaacaat gtgcc                                                   15

<210> SEQ ID NO 15
<211> LENGTH: 17
<212> TYPE: DNA
<213> ORGANISM: Saccharomyces cerevisiae

<400> SEQUENCE: 15
cggatcactc cgaaccg                                                 17

<210> SEQ ID NO 16
<211> LENGTH: 17
<212> TYPE: DNA
<213> ORGANISM: Saccharomyces cerevisiae

<400> SEQUENCE: 16
cggagatatc tgcgccg                                                 17

<210> SEQ ID NO 17
<211> LENGTH: 16
<212> TYPE: DNA
<213> ORGANISM: Saccharomyces cerevisiae

<400> SEQUENCE: 17
ggcggtcttt cgtccg                                                  16

<210> SEQ ID NO 18
<211> LENGTH: 17
<212> TYPE: DNA
<213> ORGANISM: Saccharomyces cerevisiae

<400> SEQUENCE: 18
cggggcagac tattccg                                                 17

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: adaptor
      sequence - Watson strand

<400> SEQUENCE: 19
ctagttaggt aatgatgca                                               19

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: adaptor
      sequence - Crick strand

<400> SEQUENCE: 20
```

-continued

```
tcattaccta a                                                    11

<210> SEQ ID NO 21
<211> LENGTH: 48
<212> TYPE: DNA
<213> ORGANISM: Simian virus 40

<400> SEQUENCE: 21
cgattcagcc atatcacatt tgtagaggtt ttacttgctt taaaaaac            48

<210> SEQ ID NO 22
<211> LENGTH: 48
<212> TYPE: DNA
<213> ORGANISM: Simian virus 40

<400> SEQUENCE: 22
cggtttttta aacgaagtaa aacctctaca taagtgatag gtctgaat            48
```

HIGH COPY NUMBER RECOMBINANT EXPRESSION CONSTRUCT FOR REGULATED HIGH-LEVEL PRODUCTION OF POLYPEPTIDES IN YEAST

This invention was made with the support of the National Institute of Health under grant R01 GM27925-19. The United States government has certain rights in this invention.

BACKGROUND OF THE INVENTION

1. Field of the Invention

This invention relates to improving production levels of endogenous or heterologous polypeptides expressed in yeast by recombinant genetic means. In particular, the invention relates to the construction of high copy number recombinant expression constructs that produce elevated levels of stoichiometrically balanced amounts of trans-acting transcription factors that induce transcriptional activity in yeast. Specifically, the invention provides recombinant constructs encoding trans-acting transcription factors that regulate inducible expression of endogenous or heterologous polypeptides that are operatively linked to and expressed by regulatable promoters comprising cis-acting control elements responsive to said trans-acting transcription factors. The recombinant expression constructs of the invention express the encoded trans-acting transcription factors in amounts stoichiometrically-balanced to maintain the relative amounts thereof when expressed at elevated levels. The invention further provides methods for making modified yeast cells comprising the recombinant expression constructs of the invention. Also provided by the invention are yeast cells comprising said recombinant expression constructs of the invention. The invention provides methods for inducing high-level expression of endogenous or heterologous polypeptides in yeast cells containing the recombinant expression constructs of the invention. In certain embodiments, nucleic acid sequences encoding the endogenous or heterologous polypeptides and operatively linked to regulatable promoters comprising said cis-acting control elements are contained in recombinant expression constructs that also encode said trans-acting transcription factors. In alternative embodiments, nucleic acid sequences encoding the endogenous or heterologous polypeptides and operatively linked to regulatable promoters comprising said cis-acting control elements are contained in recombinant expression constructs separate and distinct from the recombinant expression constructs that encode said trans-acting transcription factors. In said alternative embodiments, the invention provides yeast cells comprising recombinant expression constructs encoding said trans-acting factors and also said recombinant expression constructs encoding said endogenous or heterologous polypeptides, whereby the abundance of each of the recombinant expression constructs in a substantial proportion of said cells is sufficiently high so as to provide high level production of the polypeptides encoded therein. The invention also provides polypeptides produced using the methods, constructs, and modified yeast cells of the invention.

2. Background of the Invention

Yeast, such as *Saccharomyces cerevisiae*, is an established host for expression of a variety of exogenously introduced, heterologous polypeptides using recombinant genetic technology. Expression levels of such recombinant polypeptides in yeast can reach levels greater than 10% of total cellular protein. Yeast is also a safe source of proteins for human and livestock consumption or for the production of therapeutic polypeptides. These properties make yeast a particularly useful host for genetic engineering and recombinant protein expression.

Expression of heterologous polypeptides in yeast has been accomplished in the prior art using recombinant expression constructs encoding the structural gene for the polypeptide to be expressed operatively linked to transcriptional control elements. Recombinant expression constructs containing these sequences also typically contained sequences allowing selection and amplification in both yeast and *E. coli* (Broach et al., 1979, *Gene* 8: 121–133; Rose and Broach, 1990, *Methods Enzymol.* 185: 234–279; Broach and Hicks, 1980, *Cell* 21: 501–508; Bolivar et al., 1977, *Gene* 2: 95–113). Of particular utility have been recombinant expression constructs containing the 2-micron circle plasmid of *S. cerevisiae* and the *S. cerevisiae* leu2- variant of the LEU2 gene allele. (Broach et al., 1979, *Gene* 8: 121–133; Rose and Broach, 1990, *Methods Enzymol.* 185: 234–279; Erhart and Hollenberg, 1983, *J. Bacteriol.* 156: 625–635). Such recombinant expression constructs have been reported to attain copy numbers of 100 to 500 or more per cell in yeast cells transformed therewith that were lacking the native 2-micron circle plasmid and were cultured in leucine-deficient growth media. High-level expression of polypeptides encoded in such recombinant expression constructs is possible because selection in leucine-deficient media in the presence of the inefficiently-selected leu2-d allele selects for yeast cells containing high copy numbers of the construct. An example of such a recombinant expression construct is the plasmid pC1/1 (See FIG. 2, Irani et al., 1987, *Mol. Cell Biol.* 7: 1233–1241).

Cis-acting elements and trans-acting factors of regulons such as the galactose regulon are useful for constructing recombinant expression constructs, wherein recombinant polypeptide expression can be induced and regulated in yeast cells transformed therewith. Particularly useful embodiments of such transformed yeast cells contain recombinant expression constructs in which expression is induced by culture conditions (e.g., by temperature, density, or the presence of a metabolite, nutrient, or other small molecule). Promoters activated by trans-acting factors from the galactose regulon are well known to be useful for inducing expression of recombinant polypeptides in yeast (Broach et al., 1979, *Gene* 8: 121–133). Promoters isolated in particular from the GAL1, GAL7 and GAL10 genes of the *S. cerevisiae* galactose regulon have been used extensively to achieve regulated expression of endogenous and heterologous polypeptides in yeast. These promoters are induced by addition of galactose to the culture media, and thus provide a cheap, non-toxic and convenient way to induce recombinant polypeptide expression.

The mechanisms that operate in galactose regulation of the GAL1, GAL7, and GAL10 promoters have been intensively studied (Johnston and Carlson, in *The Molecular and Cellular Biology of the Yeast Saccharomyces: Gene Expression*. Vol. 11: 193–281, 1992; Reece and Platt, 1997, *Bioessays* 19: 1001–1010). These promoters show little or no transcriptional activity and nearly undetectable levels of the GAL1, GAL7 and GAL10 gene transcripts or proteins in yeast cells cultured in the absence of galactose. However, within a few minutes after adding galactose to the yeast cell medium culture, the GAL1, GAL7 and GAL10 promoters are fully activated, resulting in greater than a 1000-fold increase in transcriptional activity (Johnston and Carlson, in *The Molecular and Cellular Biology of the Yeast Saccharomyces: Gene Expression*, Vol. 11: 193–281, 1992; Reece and Platt, 1997, *Bioessays* 19: 1001–1010).

This rapid and dramatic galactose induction of these promoters is known to be mediated by a protein complex consisting of three galactose regulon trans-acting factors: the proteins Gal3, Gal4 and Gal80 (see FIG. 1). The Gal4 protein binds to a specific seventeen base pair regulatory element (termed UASgal) upstream of the each of the GAL genes (Johnston and Carlson, in *The Molecular and Cellular Biology of the Yeast Saccharomyces: Gene Expression*, Vol. 11: 193–281, 1992; Reece and Platt, 1997, *Bioessays* 19: 1001–1010). In the absence of galactose in the culture media, the Gal4 protein binds to the UASgal binding site, but does not induce transcription (Koh et al., 1998, *Molecular Cell* 1: 895–904; Wu, et al., 1996, *EMBO J.* 15: 3951–3963); in this state, the Gal4 protein is tightly associated with another member of the complex, Gal80. In the presence of galactose, the Gal3 protein binds to Gal80, altering the Gal80-Gal4 protein interaction. This results in transcriptional activation of the GAL promoters by Gal4 (Johnston and Carlson, in *The Molecular and Cellular Biology of the Yeast Saccharomyces: Gene Expression*, Vol. 11:193–281, 1992; Reece and Platt, 1997, *Bioessays* 19: 1001–1010; Torchia and Hopper, 1986, *Genetics* 113: 229–246; Lue et al., *Mol. Cell Biol.* 7: 3446–3451, 1987; Suzuki-Fujimoto et al., 1996, *Mol. Cell Biol.* 16: 2504–2508).

Strong evidence indicates that proper regulation of transcription from galactose-inducible promoters requires a stoichiometric balance in the relative abundancies of the Gal3, Gal4 and Gal80 proteins (Johnston and Hopper, 1982, *Proc. Natl. Acad. Sci. USA* 79: 6971–6975; Hashimoto et al., 1983, *Mol. Gen. Genet.* 191: 31–38; Nogi et al., 1984, *Mol Gen. Genet.* 195: 29–34; Bhat and Hopper, 1992, *Mol. Cell Biol.* 12: 2701–2707). The natural abundance of each of these proteins in yeast cells is low, particularly that of Gal4 (Laughon and Gesteland, 1982, *Proc. Nat'l. Acad. Sci. U.S.A.* 79: 6827–6831). Gal4 has also been shown to be rate-limiting for expression of native, chromosomal, single-copy genes expressed via GAL promoters in the galactose regulon, i.e., the level of transcriptional activity of the structural genes of the galactose regulon depends on the amount of Gal4 produced in the cell (Johnston and Hopper, 1982, *Proc. Natl. Acad. Sci. USA* 79: 6971–6975). The extremely low level of Gal4 in native yeast cells has proved to be a serious impediment to the use of high-copy number, GAL promoter-containing recombinant expression constructs to produce high levels of recombinant polypeptides.

In addition, it turns out that Gal4 cannot simply be over-expressed to overcome these difficulties. In doing so, the normal stoichiometric balance between Gal4, Gal80 and Gal3 is upset, and Gal4 becomes a constitutive transcriptional element that stimulates expression in the absence of galactose in the culture media (Johnston and Hopper, 1982, *Proc. Natl. Acad. Sci. USA* 79: 6971–6975). An additional complication is that high levels of the Gal4 protein, unbalanced by corresponding stoichiometric levels of at least the Gal80 protein, are toxic to the cell (Laughon et al., 1984, *Molec. Cell. Biol.* 4: 268; Gill & Ptashne, 1988, *Nature* 334: 721–724; Mylin et al., 1990, in *Methods in Enzymology*, Colowick and Kaplan, eds., Vol. 185, pp. 297–308; Martegani et al., 1993, *Yeast* 9: 575–582; Mylin & Hopper, 1996, in *Methods in Molecular Biology, Tuan, ed., Vol.* 62). This loss of appropriate repression by Gal80 protein in constructs depending on Gal4 transcriptional activation seriously limits the usefulness of yeast cells transformed therewith, because it is advantageous to suppress transcriptional activity of the recombinant polypeptide until the cells reach high densities. This is often crucial in achieving high-level production of recombinant polypeptides, the expression of which often physiologically stresses the host cell and limits cell growth and division if recombinant polypeptides are produced at high levels prematurely. In fact, negative selective growth pressure against yeast cells producing such recombinant proteins results in a preponderance of cells in the culture that do not express high levels of the protein, thus rendering the culture an uneconomical source of recombinant polypeptide.

The prior art contains one attempt known to the present inventor at overcoming these intrinsic limitations of using galactose regulon trans-acting factors to provide regulated production of a recombinant polypeptide. This attempt consisted of expressing Gal4 using the GAL10 gene promoter (Mylin et al., 1990, *Methods in Enzymology* 185: 297–308). Unfortunately, the unusually high levels of Gal4 protein produced in these cells, unbalanced by Gal80 protein, were toxic: upon galactose induction, cell growth ceased and sustained production of recombinant polypeptide was not possible.

Thus, there is a need in the art for recombinant expression constructs and methods for inducing and regulating sustained high-level production of recombinant polypeptides in yeast.

SUMMARY OF THE INVENTION

The present invention provides methods, reagents and recombinant yeast cells capable of sustained, high level production of recombinant polypeptides.

The invention provides novel recombinant expression constructs that produce robust, high-level expression of nucleic acids encoding endogenous or heterologous polypeptides in yeast. The invention specifically provides novel high copy number recombinant expression constructs that express stoichiometrically-balanced levels of trans-acting transcription factors at levels higher than these factors are expressed in native yeast cells. These constructs of the invention produce high-level expression of polypeptides whose expression is regulated by a cis-acting transcription control element responsive to the trans-acting transcription factor encoded therein. In a preferred embodiment, recombinant polypeptide expression controlled by the transcription control elements encoded by the recombinant expression constructs of the invention is inducible, preferably by altering culture conditions such as adding a nutrient or metabolite to the yeast cell culture media. In preferred embodiments, the recombinant expression construct comprises nucleic acid encoding a number of trans-acting transcription factors comprising a multi-protein transcription "switch", a yeast selectable marker that provides an inefficiently selected phenotype, and a yeast origin of replication.

In a first embodiment, the recombinant expression construct encodes a plurality of trans-acting factors encoded by a yeast regulon. In preferred embodiments, the recombinant expression construct encodes a plurality of trans-acting factors of the yeast galactose regulon. In particularly preferred embodiments, the recombinant expression construct encodes the GAL4, GAL80 and GAL3 genes of the yeast galactose regulon, most preferably wherein the construct comprises one copy apiece of these trans-acting factor genes. In these embodiments, the construct produces a stoichiometrically balanced amount of the products of these genes in a yeast cell transformed therewith, that is, wherein the amounts of each of the trans-acting factors are elevated equally, so that their relative ratios are preserved as occurs in the native yeast cell. Most preferably, each of the trans-acting factors is expressed using its native promoter, so that the relative transcriptional activity of the trans-acting factor-encoding genes is maintained.

In additional preferred embodiments, the recombinant expression construct encodes a plurality of trans-acting factors of the yeast inorganic phosphate regulon. In particularly preferred embodiments, the recombinant expression construct encodes the PHO81, PHO85, PHO80, PHO2, and PHO4 genes of the yeast inorganic phosphate regulon, most preferably wherein the construct comprises one copy apiece of these trans-acting factor genes. In these embodiments, the construct produces a stoichiometrically balanced amount of the products of these genes in a yeast cell transformed therewith.

The recombinant expression constructs of the invention encode a yeast selectable marker that is inefficiently selected and requires a yeast cell expressing the selectable phenotype to contain the construct in multiple or high copy number (i.e., the number of templates must be amplified to provide sufficient production of the gene product to permit cell growth under the selection conditions). In a preferred embodiment, the inefficiently-selected selectable marker is the leu2-d allele of the yeast LEU2 gene.

The recombinant expression constructs of the invention also contain a yeast origin of replication. In a preferred embodiment, the construct contains a complete copy of the yeast 2-micron circle.

The recombinant expression constructs of the invention also advantageously encode a yeast selectable marker that is efficiently selected by addition of a selective agent to yeast cell culture media. In a preferred embodiment, the efficiently-selected selectable marker is the yeast URA3 gene.

In still further embodiments, the invention also provides recombinant expression constructs encoding a temperature-sensitive mutant allele of a trans-acting transcription factor, wherein inducible recombinant polypeptide expression is dependent on growing a culture of yeast cells transformed with the construct at a temperature non-permissive for repression. In a preferred embodiment, the non-permissive temperature is from about 30° C. to about 36° C., and the permissive temperature, under which normal repression remains intact, is from about 20° C. to about 29° C. In such embodiments, recombinant polypeptide expression is achieved by shifting the temperature of the cell culture from the lower temperature that is permissive for repression to the higher temperature that is non-permissive for repression (thereby removing repression of recombinant polypeptide expression).

In certain preferred embodiments of the invention, the recombinant expression construct also comprises a regulatable promoter comprising one or more copies of a cis-acting transcription control element responsive to the trans-acting factors. Said regulatable promoter is advantageously operatively linked to a nucleic acid encoding an endogenous or heterologous polypeptide. In preferred embodiments, the cis-acting control element is a promoter comprising a UAS-gal site (Sequence ID No. 1). In still further preferred embodiments, the regulatable promoter is the promoter of the GAL1 gene, the GAL7 gene, or the GAL10 gene.

In additional preferred embodiments, said regulatable promoter comprising a cis-acting transcription control element is positioned adjacent to a unique restriction endonuclease recognition site in the construct for cloning a nucleic acid encoding a recombinant polypeptide to be expressed. In preferred embodiments, the unique restriction site is selected from the restriction sites NotI, AatII, SacII and PmeI. In preferred embodiments, a multiplicity of unique restriction endonuclease recognition sites are arranged to comprise a polylinker moiety, whereby said multiplicity of said recognition sites are provided at a particular position in the construct and substantially adjacent to each other. Most preferably, each recognition site in the linker is unique, i.e., it does not occur anywhere else in the construct, and the linker is positioned so as not to interfere with or otherwise influence expression from any of the other components of the construct. Most preferably, the polylinker moiety is positioned to be adjacent to the regulatable promoter comprising cis-acting transcription control element, whereby insertion of a polypeptide-encoding nucleic acid at any site in the polylinker places the polypeptide-encoding nucleic acid under the transcriptional control of the regulatable promoter and the cis-acting transcription control element.

In additional, alternative embodiments, the invention provides a second recombinant expression construct comprising a regulatable promoter comprising a cis-acting transcription control element responsive to the trans-acting transcription factor(s) comprising the first recombinant expression construct, a yeast selectable marker that provides an efficiently selected phenotype, and a yeast origin of replication. In this embodiment, the efficiently-selected selectable marker of this second recombinant expression construct must be different from both the efficiently-selected selectable marker and the inefficiently-selected marker of the recombinant expression construct of the invention encoding the cognate trans-acting transcription factor(s). In this second recombinant expression construct, the regulatable promoter comprising the cis-acting transcription control element responsive to the trans-acting factors is operatively linked to a nucleic acid encoding an endogenous or heterologous polypeptide. In particularly preferred embodiments, said regulatable promoter comprising the cis-acting control element is a promoter comprising a UASgal site (Sequence ID No.1). In additional preferred embodiments, the regulatable promoter is the promoter of the GAL1 gene, the GAL7 gene, or the GAL10 gene.

In a particularly preferred embodiment, the regulatable promoter comprising said cis-acting transcription control element is positioned adjacent to a unique restriction endonuclease recognition site in the construct for cloning a nucleic acid encoding a recombinant polypeptide to be expressed. In preferred embodiments, the unique restriction site is selected from the restriction sites NotI, AatII, SacII and PmeI. In preferred embodiments, a multiplicity of unique restriction endonuclease recognition sites are arranged to comprise a polylinker moiety, whereby said multiplicity of said recognition sites are provided at a particular position in the construct and substantially adjacent to each other. Most preferably, each recognition site in the linker is unique, i.e., it does not occur anywhere else in the construct, and the linker is positioned so as not to interfere with or otherwise influence expression from any of the other components of the construct. Most preferably, the polylinker moiety is positioned to be adjacent to the regulatable promoter comprising the cis-acting transcription control element, whereby insertion of a polypeptide-encoding nucleic acid at any site in the polylinker places the polypeptide-encoding nucleic acid under the transcriptional control of the regulatable promoter comprising the cis-acting transcription control element.

The recombinant expression constructs of the invention are also advantageously provided comprising a bacterial origin of replication and a bacterial selectable marker. In preferred embodiments, the bacterial origin of replication is a colE1 origin of replication. In more preferred embodiments, the bacterial origin of replication and the bacterial selectable marker are each derived from the *E. coli* pBR322 plasmid. In further preferred embodiments, the bacterial selectable marker is an ampicillin resistance, tetracycline resistance, hygromycin resistance, neomycin resistance or chloramphenicol resistance marker. Incorporation of a bacterial replication origin and selectable marker facilitates the genetic engineering and production of the recombinant expression construct in bacterial cells.

A particularly preferred embodiment of this invention is a recombinant expression construct comprising a nucleic acid encoding a plurality of trans-acting transcription factors, a first yeast selectable marker that provides an inefficiently selected phenotype, a second yeast selectable marker that provides an efficiently selected phenotype, a yeast origin of replication, a bacterial origin of replication, a bacterial selectable marker, and one or more unique restriction endonuclease recognition sites. The recombinant expression constructs provided by the invention produce an elevated, stoichiometrically balanced amount of the trans-acting transcription factors, that is, wherein the amounts of each of the trans-acting factors are elevated to the same degree so that the different trans-acting factors are produced in the same ratios found in the native yeast cell. Most preferably, each of the trans-acting factors is expressed using its native promoter, so that the relative transcriptional activity of the trans-acting factor-encoding genes is maintained.

A preferred recombinant expression construct encodes the trans-acting transcription factors Gal4, Gal80 and Gal3; the first yeast selectable marker is URA3, the second yeast selectable marker is the leu2-d allele of the LEU2 gene; and the unique restriction sites are for the endonucleases NotI, AatII, SacII, and PmeI. In most preferred embodiments, the construct is the MEGA2 plasmid shown in FIG. 2 (ATCC Accession No. 207162). In an alternative preferred embodiment, the URA3 gene is deleted from this construct as disclosed herein, to provide the plasmid MEGA2ΔURA3.

The invention provides methods for producing yeast cells capable of inducing or sustaining high-level production of a recombinant polypeptide. In one embodiment of this aspect of the invention is provided a method comprising the steps of introducing into a yeast cell a recombinant expression construct of the invention. In a preferred embodiment, the method comprises the steps of transforming or transfecting yeast cells with a recombinant expression construct of the invention and selecting transformed or transfected yeast cells. In additional preferred embodiments, the method comprises the further step of performing an additional selection on the cells obtained in the first selection step, wherein this second selection step selects transformed or transfected yeast cells containing a multiple or high copy number of the recombinant expression construct. In preferred embodiments of this aspect of the invention, the first selection step is specific for an efficiently-selected selectable marker encoded by the recombinant expression construct contained in the yeast cell, and the second selection step is specific for an inefficiently-selected selectable marker encoded by the recombinant expression construct contained in the yeast cell.

The present invention also provides yeast cells containing a recombinant expression construct of the invention. In one aspect of this embodiment of the invention are provided yeast cells transformed or transfected by a recombinant expression construct of the invention. In a preferred embodiment of the invention, the yeast cells are *S. cerevisiae* cells. In other preferred embodiments of the invention, the yeast cell transformed or transfected by the constructs is selected from the genera Saccharomyces, Kluveromyces or Pichia. In preferred embodiments, the yeast cells contain a multiple or high copy number of the recombinant expression construct, most preferably wherein the construct is MEGA2. In additional preferred embodiments, the yeast cells express an elevated, stoichiometrically-balanced amount of the trans-acting transcription factors encoded by the recombinant expression construct contained therein. In other preferred embodiments, the recombinant expression construct contained in the yeast cells additionally encodes an exogenous or heterologous polypeptide operatively linked to and under the transcriptional control of a regulatable promoter comprising cis-acting transcription control elements responsive to the trans-acting transcription factors encoded by the recombinant expression construct contained therein. In additional, alternative preferred embodiments, the yeast cells contain a second recombinant expression construct comprising an exogenous or heterologous polypeptide operatively linked to and under the transcriptional control of a regulatable promoter comprising a cis-acting transcription control elements responsive to the trans-acting transcription factors encoded by the first recombinant expression construct contained therein. In additional preferred embodiments of this aspect of the invention, each of the first and second recombinant expression constructs of the invention comprising said yeast cells encode an efficiently-selected selectable marker, whereby the efficiently-selected selectable marker of the first recombinant expression construct is different from the efficiently-selected selectable marker of the second recombinant expression construct. Most preferably, the first recombinant expression construct encoding a plurality of trans-acting transcription factors further comprises an inefficiently-selected selectable marker, so that the first recombinant expression construct is present in the yeast cells at multiple or high copy number, preferably wherein the copy number of the first recombinant expression construct is as high or higher than the copy number of the second recombinant expression construct.

The present invention also provides methods for efficiently and economically increasing the level of recombinant polypeptide production in yeast. In this aspect, the invention provides a method for producing elevated levels of recombinant polypeptide in a yeast cell wherein the yeast cell is a cell into which a recombinant expression construct of the invention has been introduced. In preferred embodiments, said yeast cells contain multiple or high copy number of a recombinant expression construct of the invention encoding a plurality of trans-acting transcription factors and further encoding the recombinant polypeptide to be expressed, operatively linked to a regulatable promoter comprising a cis-acting transcription control element responsive to said trans-acting factors. The methods provided by the invention comprise the step of growing the yeast cells to an appropriate cell density, and then inducing expression of the recombinant polypeptide. Recombinant polypeptide expression is induced by altering cell culture conditions, such as temperature or density, or by adding an effective amount of a nutrient, metabolite or other small molecule (generically termed an "inducing agent" herein) into the culture media. In a particular and preferred aspect, the method comprises the step of inducing recombinant polypeptide expression by adding galactose to the yeast culture media in a yeast cell culture wherein the yeast cells comprise a recombinant expression construct encoding trans-acting transcription factors Gal3, Gal4 and Gal 80 of the yeast galactose regulon, and a regulatable promoter comprises a cis-acting transcription control element responsive thereto operatively linked to a nucleic acid encoding the recombinant polypeptide to be expressed. In a second particular and preferred aspect, the method comprises the step of inducing recombinant polypeptide expression by changing the temperature at which the yeast cells are grown from a temperature permissive for normal repression to a temperature that is non-permissive for repression, in yeast cells comprising a recombinant expression construct encoding a temperature-sensitive embodiment of a trans-acting transcription factor.

In additional preferred embodiments of the methods of the invention, the yeast cells express an elevated, stoichiometrically-balanced amount of the trans-acting transcription factors encoded by the recombinant expression construct contained therein. In other preferred embodiments, the recombinant expression construct contained in the yeast cells also encodes an exogenous or heterologous polypeptide operatively linked to and under the transcriptional control of a regulatable promoter comprising cis-acting transcription control elements responsive to the trans-acting transcription factors encoded by the recombinant expression construct contained therein. In additional, alternative preferred embodiments, the yeast cells contain a second recombinant expression construct comprising a nucleic acid encoding an exogenous or heterologous polypeptide operatively linked to and under the transcriptional control of a regulatable promoter comprising cis-acting transcription control elements responsive to the trans-acting transcription factors encoded by the first recombinant expression construct contained therein. In additional preferred embodiments of this aspect of the invention, each of the first and second recombinant expression constructs of the invention comprising said yeast cells encode an efficiently-selected selectable marker, whereby the efficiently-selected selectable marker of the first recombinant expression construct is different from the efficiently-selected selectable marker of the second recombinant expression construct. Most preferably, the first recombinant expression construct encoding a plurality of trans-acting transcription factors further comprises an inefficiently-selected selectable marker, so that the first recombinant expression construct is present in the yeast cells at multiple or high copy number, preferably wherein the copy number of the first recombinant expression construct is as high or higher than the copy number of the second recombinant expression construct. In a particularly-preferred embodiment of the inventive methods, the trans-acting transcription factors encoded by the recombinant expression construct of the invention contained in the yeast cells are Gal4, Gal80 and Gal3, and recombinant polypeptide expression is induced by the addition of an effective amount of galactose into the media.

Specific preferred embodiments of the present invention will become evident from the following more detailed description of certain preferred embodiments and the claims.

DETAILED DESCRIPTION OF THE PREFERRED EMBODIMENTS

Figure 1:
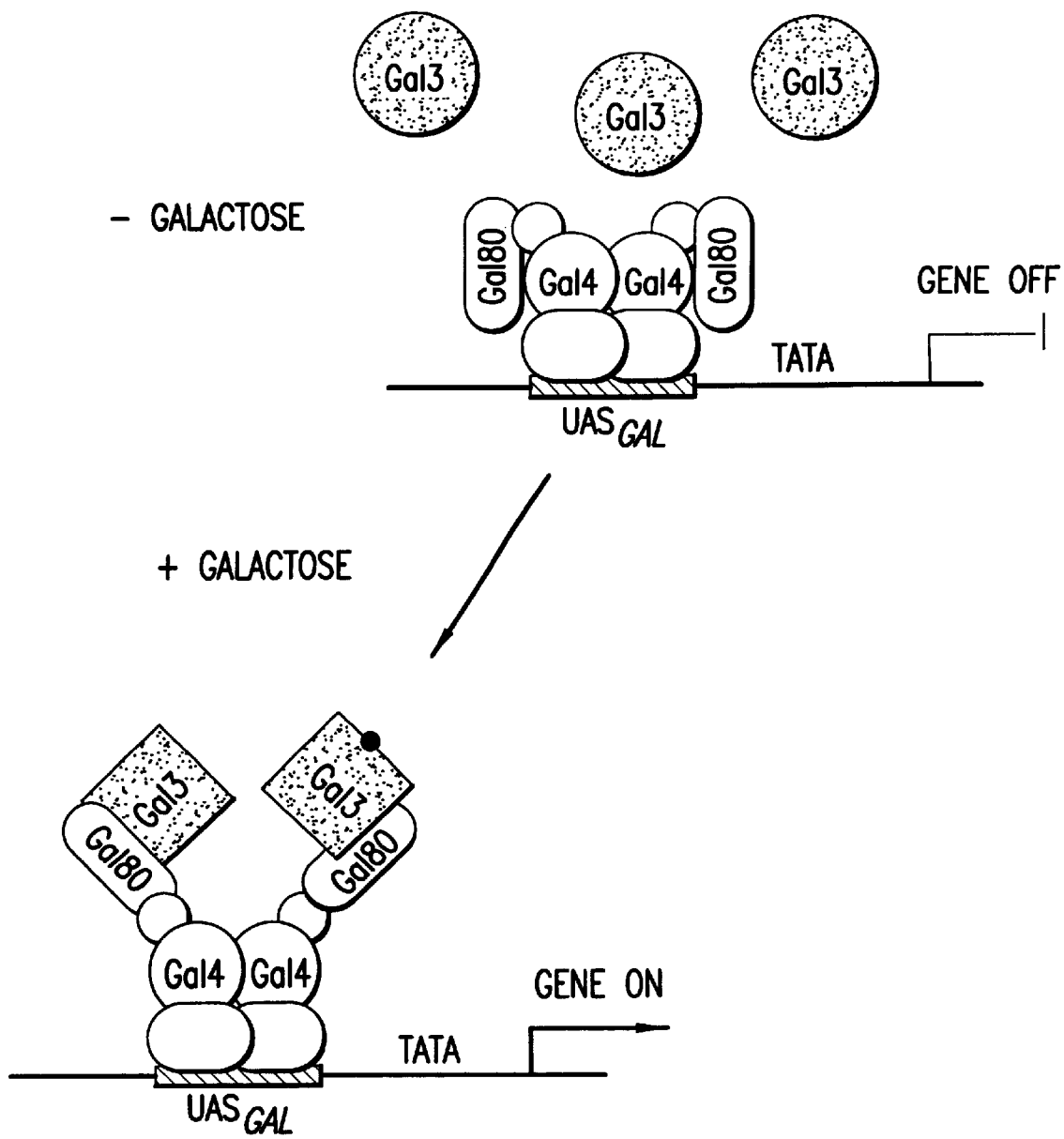
FIG. 1 illustrates galactose-induced transcriptional activation of the Gal4-Gal80-Gal3 transcription factor complex.

For the purposes of this application, the term "heterologous" will be understood to describe nucleic acids introduced into a cell by genetic engineering or other means, thereby providing the cell with the capacity to express a hitherto unexpressed polypeptide derived from the same or another cell or cell type, and the polypeptide produced thereby.

The terms "expression construct" and "recombinant expression construct" will be understood to describe genetically-engineered nucleic acid sequences encoding at a minimum an origin of replication, a selectable marker and a gene or polypeptide-encoding nucleic acid of interest to be expressed in a recipient host cell.

The term "multiple copy number" or "high copy number" will be understood to describe a characteristic of a recombinant expression construct present in a host cell in greater than a single copy per cell. In particular, the term will be understood to imply that copy number of the construct inside the cell is not dependent upon or restricted to the copy number of cellular genetic material. More preferably, a "multiple copy number" or "high copy number" construct will be understood to be a construct whose replication is highly amplified within a host cell. As used herein the number of copies contained in a cell that are described as "multiple copy number" or "high copy number" is from about 10 to about 700 copies per cell.

The term "regulatable promoter" is intended to encompass DNA sequences that mediate transcription of a nucleic acid in a cell. Representative and exemplary promoters comprise sequences such as AT-rich sequences termed "TATA" boxes, and additional sequences comprising the sequence "CAAT" that are recognized as mediating the interaction of the nucleic acid of the promoter with protein factors such as RNA polymerase. In addition, regulatable promoters are distinguished from promoters that are not regulatable in that regulatable promoters are operatively linked to "cis-acting transcription control elements" that will be understood to be nucleic acid sequences that regulate or control transcription of a polypeptide-encoding nucleic acid. As used herein, the term "cis-acting transcription control element" is particularly directed to nucleic acid sequences that make said regulatable promoter "inducible," as that term is defined herein below. Said regulatable promoters of the invention comprising said cis-acting transcription control elements are operatively-linked to polypeptide-encoding nucleic acids and control transcription thereof in a cell, most preferably a yeast cell, into which a recombinant expression construct of the invention has been introduced. Most preferably, the transcription control of the regulatable promoters of the invention is mediated by interaction between the cis-acting transcription control elements with the trans-acting transcription factors encoded by the recombinant expression constructs of the invention. An example of a regulatable promoter is a GAL promoter from any of the regulated genes of the yeast galactose regulon.

The term "operatively linked" is intended to describe covalent linkage between nucleic acids wherein the quality, position and proximity of the linkage ensures coupled replication and is sufficient and appropriate to be recognized by trans-acting transcription factors and other cellular factors whereby polypeptide-encoding nucleic acid is efficiently expressed under appropriate conditions.

The term "trans-acting transcription factors" as used herein is intended to encompass polypeptides that, either themselves or as part of a multiprotein complex, recognize their cognate cis-acting transcription control elements and thereby mediate expression, particularly "inducible" expression as defined herein, of polypeptide-encoding nucleic acids operatively linked thereto. In preferred embodiments, the trans-acting transcription factors encoded by the recombinant expression constructs of the invention are derived from naturally-occurring regulons and thereby permit expression of recombinant polypeptides to be induced by altering cell culture conditions, for example, by adding an effective amount of the inducing agent into the culture media. In preferred embodiments, the trans-acting factors encoded by the recombinant expression constructs of the invention comprise Gal4, Gal80 and Gal3 proteins of the yeast galactose regulon, and recombinant polypeptide expression is induced by adding an effective amount of galactose to the yeast culture media.

The term "inducible" will be understood to mean that activation of transcriptional activity of a regulatable promoter comprising a cis-acting transcriptional control element is initiated or increased by a stimulus. Preferably, the inducing stimulus is an alteration in cell culture conditions, including but not limited to a change in temperature, density or the presence of a small molecule such as a metabolite, nutrient, or other small molecule to the culture media. In a preferred embodiment, the inducing stimulus is the addition of an effective amount of galactose to a yeast culture comprising a recombinant expression construct of the invention encoding a plurality of trans-acting factors derived from the yeast galactose regulon. In another preferred embodiment, the inducing stimulus is alteration of the temperature of a yeast culture from a temperature permissive for repression to a temperature non-permissive for repression.

For the purposes of this invention, the term "stoichiometrically balanced" is intended to mean that the relative amounts (or ratios) of each of the number of trans-acting transcription factors encoded by one or more recombinant expression constructs comprising a yeast cell of the invention are the same as the relative amounts or ratios of said trans-acting transcription factors expressed in native yeast cells (i.e., the ratios of the proteins are present in the same molecular ratios as are present endogenously). More particularly, the term is intended to mean that, although overexpressed as the result of the genetic engineering techniques disclosed herein, the relative amounts of the trans-acting transcription factors encoded by one or more recombinant expression constructs comprising a yeast cell of the invention is sufficient for said yeast cells to induce recombinant polypeptide expression when provoked by the proper inducing stimulus, and that the overexpression of these trans-acting transcription factors does not prohibit yeast cell growth or recombinant polypeptide expression. It will be further understood that production of a "stoichiometrically balanced" amount of a complex of transcription factors can be accomplished by any means known to one of skill in the recombinant genetic arts. These means include using recombinant expression constructs encoding inefficiently-selected selectable markers, wherein the copy number of the construct is amplified in the yeast cell to provide a sufficient amount of the protein encoded by the marker to express the selectable phenotype, thereby co-amplifying genes encoding a plurality of trans-acting transcription factors. It is also intended to encompass recombinant expression constructs containing additional copies of underexpressed members of the complex, and using heterologous promoters, enhancers or other transcriptional control elements to differentially increase expression levels of any under-expressed member of the complex, to produce a stoichiometrically balanced amount of each of the trans-acting factors.

For the purposes of this invention, with regard to polypeptide expression, the terms "elevated" or "elevated expression" are intended to indicate that the amount of the polypeptide produced in a cell, preferably a yeast cell and most preferably a yeast cell transformed with at least one of the recombinant expression constructs of the invention, is higher, more preferably much higher, that the amount of the polypeptide produced either natively or using other recombinant expression constructs. For the trans-acting transcription factors of the constructs of the invention, the term is intended to reflect the increased expression levels associated with amplification due to selection of the inefficiently-selected selectable marker. For endogenously produced polypeptides, the term is intended to mean increased expression compared with endogenous expression levels. For heterologous polypeptides, the term is intended to reflect increased production of said heterologous polypeptides compared with conventional recombinant or genetic engineering-related expression vectors, systems and methods.

The present invention provides nucleic acids, recombinant expression constructs, yeast cells, reagents and methods for increasing and sustaining high-level production of polypeptides in yeast. For the purposes of this invention, the term "high-level production" is intended to encompass a ten-to one hundred-fold increase in the amount of recombinant polypeptide produced when compared with production of the polypeptide in native yeast cells comprising native amounts of the trans-acting factors encoded by the recombinant expression constructs of the invention.

The recombinant expression constructs of the invention comprise nucleic acids encoding a plurality of trans-acting transcription factors. In a preferred embodiment, the construct encodes a plurality of trans-acting transcription factors derived from the galactose regulon, most preferably comprising Gal3, Gal4 and Gal80.

In additional embodiments, other yeast genes or regulon genes can be used in the construction of the recombinant expression constructs of the invention. In one example, a recombinant expression construct comprising genes encoding the Pho81p, Pho85p, Pho80p, Pho2p, and Pho4p complex, which responds to inorganic phosphate levels, is useful for regulating heterologous polypeptide expression mediated by transcription from a PHO5 gene promoter and cis-acting sequences regulated by the Pho4p and Pho2p transcription factors. (See Hirst et al., 1994, *EMBO J.* 13: 5410–5420).

In another example, a recombinant expression construct comprising the gene encoding the Hap1p protein, which responds to heme and oxygen levels, is useful for regulating heterologous polypeptide expression by transcription from a cyc1 or cyc7 promoter and containing a Hap1 protein binding site (See Kwast et al., 1998, *J. Exp. Biol.* 201: 1177–1195; Zhang & Guarante, 1995, *EMBO J.* 14: 313–320; Pfeifer et al., 1989, *Cell* 56: 291–301).

Additional examples include the Snf1p-Sip4p complex, which responds to glucose levels (Lesage et al., 1996, *Molec. Cell. Biol.* 16: 1921–1928); the Ssn6p-Tup1p complex, which responds to glucose levels (Treitel & Carlson, 1995, *Proc. Natl. Acid. Sci. USA* 92: 3132–3136); the Gcd1 p-Gcd2p-Gcn3p-Gcn4p complex, which responds to amino acid levels (Hinnebusch, 1992, *Molecular Biology of Yeast Saccharomyces Gene Expression* (Jones, ed.), CSHLP: NY); and the Ste5p-Ste11p-Ste7p-Kss1p-Fus3p-Ste12p complex, which regulates Ste1p transcription activation of alpha-factor inducible gene expression (Sprague & Thorner, 1992, *Molecular Biology of Yeast Saccharomyces Gene Expression* (Jones, ed.), CSHLP: NY).

The recombinant expression constructs of the invention comprise a yeast origin of replication. In a preferred embodiment, the origin of replication comprises a complete yeast 2 micron circle. The 2-micron circle is an endogenous yeast plasmid that naturally occurs at approximately 100 copies per cell (Broach, 1983, *Methods Enzymol.* 101: 307–325). The 2 micron circle permits autonomous replication in both yeast that contain an endogenous 2-micron circle plasmid (cir$^+$) and those that lack an endogenous 2-micron circle plasmid (cir$^\circ$) (Irani et al., 1987, *Mol. Cell Biol.* 7:1233–1241).

In additional preferred embodiments, the yeast origin of replication is derived from any yeast vector, including but not limited to Ycp-CEN vectors (which attain 1–2 copies/ cell), normal ARS-containing vectors (which are multiple copy vectors), and Yrp and Yep vectors (which attain 7–20 copies/cell); these vectors are well-known in the art (see Parent & Bostian, 1990, "Recombinant DNA Genetics: 1. Vectors," in *THE YEASTS*, 2$^{nd}$ ed., vol. 6: Yeast Genetics (Wheals & Rose, eds.), Academic Press: New York).

The recombinant expression constructs of the invention comprise an inefficiently-selected yeast selectable marker. For the purposes of this invention, the term "inefficiently-selected selectable marker" is intended to encompass alleles of genes, most preferably yeast genes, that produce a protein having a diminished capacity to produce the phenotype associated with its genetic locus. An illustration of this type of allele is one having a reduced catalytic capacity, so that a much smaller amount of a metabolite, most preferably an anabolic metabolite such as a precursor or intermediate in the production of an amino acid, a nucleotide, a carbohydrate, a lipid, or a metabolically-necessary small molecule such as a co-factor, is produced by the inefficiently-selected allele than is produced by another allele at the same locus that is not inefficiently-selected. As a consequence, a larger amount of the protein encoded by an inefficiently-selected allele must be produced in order to express the phenotype. Alternatively, inefficiently-selected selectable markers include mutant alleles of genes, most preferably yeast genes that produce a selectable protein, wherein the gene is expressed at diminished levels due to, for example, a mutation in a cis-acting sequence such as a promoter, enhancer or other cis-acting sequence. In these embodiments, as well as in embodiments wherein a defective marker protein is produced, the required overproduction of the protein encoded by the marker is preferably achieved according to the invention by amplifying the plasmid episome comprising the inefficiently-selected allele. In a preferred embodiment, the second, inefficiently-selected yeast selectable marker is the leu-2d allele of the LEU2 gene.

The recombinant expression constructs of the invention optionally comprise nucleic acid encoding a second, efficiently-selected yeast selectable marker. In a preferred embodiment, the efficiently-selected selectable marker is URA3. In additional preferred embodiments, the efficiently-selected selectable marker include but are not limited to HIS3, HIS4, ADE2, ADE5,7, LYS2, LEU2, URA3, TRP1 and CUP1.

The recombinant expression constructs of the invention can be prepared in yeast cells, wherein recombinant constructs are selected using the selectable markers comprising said constructs. Alternatively and advantageously, the recombinant expression constructs of the invention are prepared in bacterial cells, and for this purpose advantageously comprise a bacterial origin of replication. In a preferred embodiment, the bacterial origin of replication is a colE1 origin, most preferably derived from the bacterial plasmid pBR322. In said embodiments, the recombinant expression constructs of the invention also advantageously comprise a bacterial selectable marker. In preferred embodiments, the bacterial selectable marker is derived from the bacterial plasmid pBR322, a genetically engineered bacterial plasmid that carries an ampicillin resistance gene, a tetracyclin resistance gene, and an origin of DNA replication for autonomous replication in *E. coli* (Bolivar et al., 1977, *Gene* 2: 95–113). In preferred embodiments, the bacterial selectable marker is a tetracycline resistance marker and more preferably an ampicillin resistance marker. In additional preferred embodiments, the bacterial selectable marker includes but is not limited to a hygromycin resistance, neomycin resistance or chloramphenicol resistance marker.

In preferred embodiments of the recombinant expression constructs of the invention comprising a bacterial origin of replication and a bacterial selectable marker, construction and propagation of the constructs are advantageously achieved by cloning in bacterial cells, most preferably *E. coli* cells. In alternative embodiments, the recombinant expression constructs of the invention encode a yeast origin of replication and one or a plurality of efficiently-selected yeast selectable markers. In these embodiments, construction and propagation of the constructs are advantageously achieved by cloning in yeast cells.

The recombinant expression constructs of the invention also optionally comprise at least one unique restriction endonuclease recognition site. In preferred embodiments, the unique restriction endonuclease site is NotI recognition site, an AatII recognition site, a SacII recognition site or a PmeI recognition site. Also preferred are constructs comprising any combination thereof. In additional embodiments, the unique restriction endonuclease recognition site includes but is not limited to any restriction enzyme site comprising six or more bases in its recognition sequence, more preferably a restriction enzyme site comprising eight or more bases in its recognition sequence, and even more preferably comprising enzymes having a recognition sequence comprising an interrupted palindrome, provided that none of such sites are located within a cistron of any gene encoded by the construct. In additionally preferred embodiments, the construct contains a polylinker sequence encoding a plurality of such uniquely-occurring restriction endonuclease recognition sites. It will be recognized that location of this polylinker sequence adjacent to a GAL promoter or any other cognate regulatable promoter of the trans-acting transcription factors of the invention is advantageous for cloning a nucleic acid encoding a recombinant polypeptide into a recombinant expression construct of the invention.

The recombinant expression constructs of the invention comprise a regulatable promoter comprising a cognate cis-acting transcription control element. For the purposes of this invention, a "cognate" cis-acting transcription control element is an element responsive to the trans-acting transcription factors encoded by the recombinant expression constructs of the invention. In certain embodiments, the regulatable promoter comprising the cognate cis-acting transcription control element is part of the same recombinant expression construct that encodes the trans-acting transcription factors of the invention. In certain other embodiments, the regulatable promoter comprising the cognate cis-acting transcription control element comprises a recombinant expression construct that is separate and distinct from the recombinant expression construct that encodes the trans-acting transcription factors of the invention. In the latter embodiments, the second recombinant expression construct comprises an efficiently-selected selectable marker different from both the efficiently-selected selectable marker and inefficiently selectable marker comprising the first recombinant expression construct encoding the cognate trans-acting transcription factors.

In preferred embodiments, the cognate cis-acting transcription control element comprising the regulatable promoter of the recombinant expression constructs of the invention is the UAS gal cis-acting sequences of the galactose/melibiose regulon. The UAS gal cis-acting sequences comprise a core sequence of 17 basepairs (bp) having dyad symmetry that binds one dimer of the Gal4 protein. The core consensus sequence is:

CGGAGGACTGTCCTCCG (SEQ ID No.: 1)

(See Kang et al., 1993, *J. Biol. Chem.* 268: 9629–9635). This consensus has been derived from actual sequences of various UASgal sites found within the promoters of different galactose-regulated genes. For example, the following UASgal sites have been found in the GAL1 and GAL10 genes:

CGGATTAGAAGCCGCCG (SEQ ID No.: 2);

CGGGTGACAGCCCTCCG (SEQ ID No.: 3);

AGGAAGACTCTCCTCCG (SEQ ID No.: 4);

and

CGCGCCGCACTGCTCCG (SEQ ID No.: 5).

(See Bram & Kornberg, 1985, *Proc. Natl. Acad. Sci. USA* 82: 43–47; Giniger et al., 1985, *Cell* 40: 767–774; Carey et al., 1989, *J. Molec. Biol.* 209: 423–432; Bram et al., 1986, *EMBO J.* 5: 603–608).

The following UASgal sites have been found upstream of the GAL7 gene:

CGGACAACTGTTGACCG (SEQ ID No.: 6);

and

GCCTGTTGACAACTGGC (SEQ ID No.: 7).

(See Giniger et al., 1985, *Cell* 40: 767–774; Lorch & Kornberg, 1985, *J. Molec. Biol.* 186: 821–824; Tajima et al., 1986, *Molec. Cell. Biol.* 6: 246–256).

The following UASgal sequence has been found upstream of the MEL1 gene:

CGGCCATATGTCTTCCG (SEQ ID No.: 8).

(See Summer-Smith et al., 1985, *Gene* 36: 333–340; Bram et al., 1986, *EMBO J.* 5: 603–608).

The following UASgal sequence has been found upstream of the GAL80 gene:

CGGCGCACTCTCGCCCG (SEQ ID No.: 9).

(See Nogi et al., 1984, *Nucl. Acids Res.* 12: 9287–9298; Bram et al., 1986, *EMBO J.* 5: 603–608).

The following UASgal sites have been found upstream of the GAL3 gene:

CGCTACAATGACCCG (SEQ ID No.: 10);

and

CGGTCCACTGTGTGCCG (SEQ ID No.: 11).

(See Bajwa et al., 1988, *Molec. Cell. Biol.* 8: 3439–3447).

The following UASgal sites have been found upstream of the GAL2 gene:

TATCGGGGCGGATCACTCCGAAC(proximal) (SEQ ID No.: 12);

and

CACCGGCGGTCTTTCGTCCGTGC(distal) (SEQ ID No.: 13).

(See Bram et al., 1986, *EMBO J.* 5: 603–608);

GGAGAACAATGTGCC (SEQ ID No. 14);

CGGATCACTCCGAACCG (SEQ ID No. 15);

CGGAGATATCTGCGCCG (SEQ ID No.16);

and

CGGCGGTCTTTCGTCCG (SEQ ID No.17)

Szkutnicka et al., 1989, *J. Bacteriol.* 171: 4486–4493).

The following UASgal sequence has been found upstream of the GCY1 gene:

CGGGGCAGACTATTCCG (SEQ ID No.: 18).

(See Angermayr et al., 1997, *Molec. Gen. Genet.* 256: 682–689).

Recombinant expression constructs having regulatable promoters comprising one or more copies of any of these UASgal sequences or combinations thereof are useful for the production of elevated levels of recombinant polypeptides using the methods of the invention.

In a preferred embodiment, recombinant expression constructs of the invention encoding either a heterologous polypeptide or an endogenous polypeptide comprise a regulatable promoter comprising one or more copies of a UASgal site, wherein the regulatable promoter is operatively linked to the coding sequence of the heterologous polypeptide. In additional embodiments, the regulatable promoter operatively linked to the heterologous or endogenous polypeptide comprises more than one UASgal site; it is within the skill of those having skill in this art to determine optimum orientation, placement and number of UASgal sites particular embodiments of the regulatable promoters of the recombinant expression constructs of the invention without undue experimentation. (See Lorch & Kornberg, 1985, *J. Molec. Biol.* 186: 821–824; Tajima et al., 1986, *Molec. Cell. Biol.* 6: 246–256).

Preferred embodiments of the recombinant expression constructs of the invention comprise a nucleic acid encoding a recombinant polypeptide. Any endogenous or heterologous nucleic acid operatively linked to an inducible or regulated promoter is useful in the recombinant expression constructs of the invention. In a preferred embodiment, the recombinant polypeptide is melibiose (α-galactosidase), more preferably operatively linked to the native MEL1 gene promoter and most preferably wherein said promoter comprises one or more copies of a UASgal sequence.

In one preferred alternative embodiment, the recombinant expression construct encoding a plurality of trans-acting transcription factors further comprises a regulatable promoter comprising a cognate cis-acting transcription control element, wherein the regulatable promoter is operatively linked to a nucleic acid encoding a recombinant polypeptide to be expressed. In an alternative preferred embodiment, yeast cells containing a first recombinant expression construct of the invention encoding a plurality of trans-acting transcription factors further comprise a second recombinant expression construct comprising a regulatable promoter comprising a cognate cis-acting transcription control element operatively linked to a nucleic acid encoding a recombinant polypeptide. In said second preferred embodiments, each of the first and second recombinant expression constructs of the invention comprising said yeast cells preferably encodes an efficiently-selected selectable marker, whereby the efficiently-selected selectable marker of the first recombinant expression construct is different from the efficiently-selected selectable marker of the second recombinant expression construct. Most preferably, the first recombinant expression construct encoding a plurality of trans-acting transcription factors further comprises an inefficiently-selected selectable marker, so that the first recombinant expression construct is present in the yeast cells at multiple or high copy number, preferably wherein the copy number of the first recombinant expression construct is as high or higher than the copy number of the second recombinant expression construct.

In a preferred and exemplary embodiment, the invention provides a high copy number recombinant expression construct comprising, in operative combination, nucleic acid encoding the complete yeast 2-micron circle; an inefficiently-selected allele of the LEU2 gene, termed leu2-d; the efficiently-selected yeast marker URA3; the trans-acting transcription factors GAL4, GAL80 and GAL3; and portions of the bacterial plasmid pBR322 encoding a colE1 bacterial origin of replication and a bacterial ampicillin gene. Gal4, Gal80, and Gal3 comprise the essential components of a galactose-inducible transcription control mechanism specifically regulating GAL promoter-driven expression of recombinant polypeptides in S. cerevisiae. In one alternative embodiment, the recombinant expression construct further comprises a GAL promoter operatively linked to a nucleic acid encoding a recombinant polypeptide operatively linked to the GAL promoter. In an alternative embodiment, the yeast cells containing the a high copy number recombinant expression construct described above further comprise a second high copy number recombinant expression construct comprising a GAL promoter operatively linked to a nucleic acid encoding a recombinant polypeptide. In said second embodiments, the first recombinant expression construct preferably comprises an efficiently-selected selectable marker different from the efficiently-selected selectable marker comprising the second recombinant expression construct. Most preferably, the first recombinant expression construct encoding a plurality of trans-acting transcription factors further comprises an inefficiently-selected selectable marker, so that the first recombinant expression construct is present in the yeast cells at multiple or high copy number, preferably wherein the copy number of the first recombinant expression construct is as high or higher than the copy number of the second recombinant expression construct.

The recombinant expression constructs of the invention are preferably introduced into *Saccharomyces cerevisiae* cells. Alternatively, the recombinant expression constructs of the invention are advantageously introduced into other species within the genus Saccharomyces. Other species, strains and varieties of yeast, such as *Pichia pastoris* and *Kluyveromyces lactis* are advantageous host cells for the recombinant expression constructs of the invention; their use for such purposes is known in the prior art (Cregg et al., 1985, *Mol. Cell Biol.* 5: 3376–3385; Raymond et al., 1998, *Yeast* 14: 11–23; Sears et al, 1998, *Yeast* 14: 783–790, Tschopp et al., 1987, *Biotechnology* 5: 13–15; Sreekrishna et al., 1984, *Gene* 28: 73–81; Riley et al., 1987, *Mol. Cell Biol.* 7: 780–786; Schulz et al., 1993, *Biol. Chem.* 374: 313–318; Webster and Dickson, 1988, *Nucleic Acids Res.* 16: 8192–8193; Webster and Dickson, 1988, *Nucleic Acids Res.* 16: 8011–8027). Yeast useful in the practice of the methods of the invention include but are not limited to *S. carlsbergensis, S. diastaticus, S. oviformis, S. norbensis, S. rouxii,* and *Kluyveromyces lactis* (Adamikova 1998, et al., *Yeast* 14: 805–812; Bogdanova et al., 1998, *Yeast* 14: 1–9; Davidow et al., 1985, *Curr. Genet.* 10: 39–48; Farrar and Williams, 1988, *Trends Genet.* 4: 343–348; Gleeson et al., 1986, *J. Gen. Microbiol.* 132: 3459–3465; Hamsa et al., 1998, *Curr. Genet.* 33: 231–237; Klein and Favreau, 1988, *J. Bacteriol.* 170: 5572–5578; Roggenkamp et al., 1986, *Mol. Gene Genet.* 202: 302–308; Shammat et al., 1998, *Curr. Genet.* 33: 77–82; Suvarna et al., 1998, *Curr. Genet.* 33: 268–275; Tikhomirova et al., 1986, *Curr. Genet.* 10: 741–747). Preferably the yeast cells used according to the methods and provided by the invention carry mutations in the chromosomal genes for the efficiently-selected and for the inefficiently-selected selectable markers encoded by the recombinant expression constructs of the invention. In preferred embodiments, the yeast cells have inactivating mutations in the URA3 and LEU2 genes.

One preferred embodiment utilizes nucleic acids whose expression is driven by an inducible yeast promoter, more specifically a promoter induced by a trans-acting factor from the galactose regulon. However, the invention may also utilize nucleic acids operatively linked to non-inducible promoters and/or non-yeast promoters. Any of the endogenous Gal4 protein-activatable promoters (derived from the GAL1, GAL2, GAL7, GAL10, or MEL1 genes) or any recombinant expression construct containing a promoter activated by the trans-acting Gal4 protein factor from the galactose regulon, or Gal4-activatable promoters having synthetic UASgal sites, can be utilized to drive induced expression of polypeptides. Furthermore, induction of the promoter is not limited to use of galactose and the Gal3-Gal80-Gal4 three-component galactose-induced transcription control mechanism. For example, a gal80 temperature-sensitive mutation of *S. cerevisiae* can result in transcriptional activation of Gal4 protein-activatable promoters in response to temperature shift in the absence of galactose (Matsumoto et al., 1978, *J. Bacteriol* 134: 446–457).

In addition to the temperature-sensitive Gal4-Gal80 transcription control mechanism, a Pho80 temperature-sensitive mutation of *S. cerevisiae* can result in transcriptional activation of phosphate-regulated PHO promoters in response to temperature shift (Lemire et al., 1985, *Mol. Cell Biol.* 5: 2131–2141). The temperature-sensitive phosphate transcription control mechanism in *S. cerevisiae* comprises a complex composed of the Pho81, Pho80, Pho85, Pho4 and Pho2 proteins and a regulatable promoter comprising a cis-acting control element recognized by the Pho4 and Pho2 proteins (Hirst et al., 1994, *EMBO J.* 13: 5410–5420). Temperature shift can be used to induce transcription control elements wherein the activity of a cis-acting control element is regulated by its interactions with temperature-sensitive trans-acting transcription factors. Recombinant expression constructs containing nucleic acids encoding temperature-sensitive trans-acting transcription factors are therefore provided by the invention.

Figure 2:
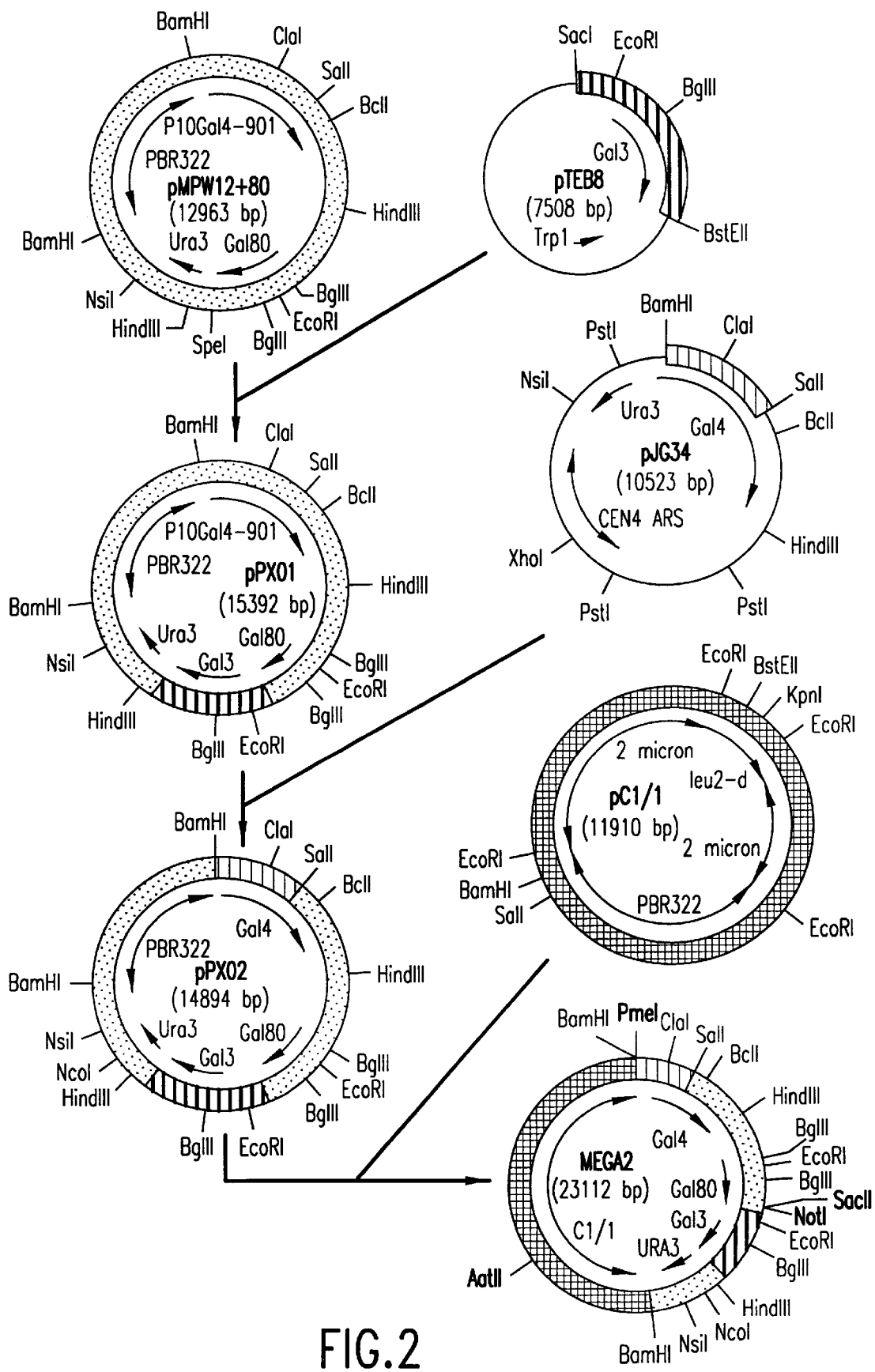
FIG. 2 illustrates the steps in the construction of the MEGA2 plasmid (ATCC Accession No. 207162) containing the GAL4 gene, the GAL80 gene, the GAL3 genes, the URA3 gene, the leu2-d allele, the pBR322 plasmid and the yeast 2-micron circle plasmid.

A preferred embodiment of the present is a composite plasmid, termed MEGA2, that contains the wild-type GAL4, GAL80, GAL3 and URA3 genes, the leu2-d allele of the LEU2 gene, pBR322 sequences and 2-micron circle plasmid sequences. Plasmid MEGA2 also contains unique restriction sites for the restriction endonucleases NotI, AatII, SacII, and PmeI. These sites are located in non-vital segments of the plasmid and are therefore useful as sites for insertion of a nucleic acid comprised of a promoter, inducible or otherwise, fused to a coding region for a polypeptide. This plasmid is illustrated in FIG. 2.

An alternative preferred embodiment of the preferred MEGA2 plasmid is provided wherein the URA3 gene is deleted from the plasmid. In this embodiment, the plasmid is termed MEGA2ΔURA3, as described more completely in Example 7 below.

In yet another alternative preferred embodiment of the preferred MEGA2 plasmid is provided wherein the GAL4 gene is modified to comprise an epitope tag. In this embodiment, the plasmid is termed MEGA3 and is described more completely in Example 8 below. It will be understood that additional preferred embodiments comprise plasmids having both the epitope tag of the MEGA3 plasmid and the URA3 deletion of the MEGA2ΔURA3 plasmid.

The GAL3, GAL4 and GAL80 genes carried on MEGA2 encode the three proteins comprising the three-component protein complex regulating galactose inducibility of transcription. All three genes are necessary to ensure that the Gal3, Gal4 and Gal80 proteins are produced at stoichiometrically balanced ratios corresponding to the naturally-occurring ratios in yeast cells expressing naturally-occurring amounts of these proteins that permit sustained transcriptional activation in the presence of galactose without causing cell death. Thus, cells harboring a plasmid bearing all three genes display normal regulatory responses, i.e., genes and transcription sequences activated by a trans-acting factor from the galactose regulon are either not expressed or expressed at very low levels in the absence of galactose and expressed at high or very high levels in the presence of galactose.

High copy number propagation of the plasmids of the invention depend upon a selection with an inefficient selectable marker such as leu2-d. Leu2-d gene is a defective allele of LEU2, the yeast gene that encodes β-isopropyl-malate synthase, an enzyme essential in the leucine biosynthetic pathway (Hsu & Kohlhaw, 1982, *J. Biol. Chem.* 257: 3941). The leu2-d allele encodes a functional β-isopropyl-malate synthase enzyme. However, due to a defective promoter, the leu2-d allele expresses very low levels of the β-isopropyl-malate synthase mRNA and polypeptide in the cell. Consequently, yeast cells bearing a defective chromosomal LEU2 gene and a plasmid extra chromosomal copy of leu2-d allele do not grow and divide readily in a leucine-deficient medium unless the copy number of the plasmid is very high (Erhart & Hollenberg, 1983, *J. Bacteriol.* 156: 625–635; Irani et al., 1987, *Mol. Cell Biol.* 7: 1233–1241). Thus, the presence of the leu2-*d allele in a recombinant expression construct of the invention, including MEGA2*, MEGA2ΔURA3 and MEGA3, in LEU2 defective host cells cultured in leucine-deficient media imposes a selection condition favoring propagation of cells harboring very high numbers of the construct (Irani et al., 1987, *Mol. Cell Biol.* 7: 1233–1241).

However, since high copy number is a condition required for growth, the use of the leu2-d allele for the primary selection of LEU2 defective yeast cells that have been transformed or transfected by a recombinant expression construct of the invention such as the MEGA2 plasmid is highly inefficient. Selection for leu2-d using standard yeast transformation protocols results in very low transformation efficiencies and long incubations (on the order of 6 to 7 days for the detection of colonies on nutrient agar plates lacking leucine). In contrast, the URA3 gene is a yeast gene encoding orotidine-5'-phosphate decarboxylase, an essential enzyme in the uracil biosynthetic pathway (Broach 1983, *Methods Enzymol.* 101: 307–325). The URA3 gene provides rapid and reliable selection for yeast cells carrying a defective chromosomal URA3 gene that have been transformed or tranfected by a recombinant expression construct of the invention such as the MEGA2 plasmid. Standard yeast transformation protocols and URA3-based selection yield the desired efficiency of colony formation and colony detection within 2 to 3 days, depending on yeast host strains. In embodiments lacking URA3, such as MEGA2ΔURA3, inefficient selection protocols are required for cell selection and growth.

In the practice of the methods of the invention for using the recombinant expression constructs of the invention to produce elevated levels of endogenous or heterologous recombinant polypeptides, a recombinant expression construct of the invention is introduced into a yeast host cell of any host yeast strain having genotype ura3, leu2 (preferably, but not necessarily, ura3-52 and leu2-2-112) and either cir$^+$ or cir°. Cir° strains are preferred when the objective is to achieve the highest possible plasmid copy number for attaining very high-level polypeptide expression (Irani et al., 1987, *Mol. Cell Biol.* 7: 1233–1241). Yeast transformants are selected on uracil-deficient media agar plates for the URA3$^+$ phenotype. A single colony obtained thereby is then inoculated into uracil-deficient liquid media containing glucose, in addition to other essential components, to generate a starter culture of the desired size for subsequent use as an inoculum for scale-up culture. The scale-up culture medium contains non-fermentable carbon sources, such as glycerol or lactic acid, and preferably is leucine-deficient. In leucine-deficient media, cells harboring very high copy levels of recombinant expression constructs containing the leu2-d allele, such as the MEGA2 and MEGA2ΔURA3 plasmids will be selected. Cells are grown on glycerol-lactic acid containing leucine-deficient liquid medium to early log phase. During this first phase of growth, the cells do not grow and divide rapidly due to the leucine deficiency. At the onset of early mid-log phase, complete media, such as yeast extract and bactopeptone, is added to provide nutrient conditions for more robust cell growth and propagation. When the cell density of the culture reaches late middle to late-log phase density, the inducing agent is added; when using the MEGA2 or MEGA2ΔURA3 plasmids, galactose is added to a final concentration of from about 0.02% to 0.2% g/mL, more preferably about 0.1% to 0.2% g/mL. In order to maintain induction for several hours when the plasmid contains a GAL promoter gene, e.g. GAL1, GAL7, or GAL 10, galactose concentrations up to 0.2% g/mL are desirable. Following galactose addition, the culture is incubated for four or more hours, after which time the cells are harvested by centrifugation. For intracellular proteins, the cells are processed by breakage for recovery of the desired protein. For secreted proteins, the supernatant of the centrifuged cell harvest is taken for recovery of the desired protein.

The following Examples illustrate certain aspects of the above-described invention and advantageous results thereof. The following examples are shown by way of illustration and not by way of limitation. The disclosure of each reference cited herein explicitly incorporated by reference.

EXAMPLE 1

Preparation of Plasmid pTEB8 Containing the Yeast GAL3 Gene

Plasmid pTEB8, the immediate source of the GAL3 gene used in constructing plasmid MEGA2, was constructed as follows. DNA containing the GAL3 gene was obtained from plasmid pT1-3B, a high-copy shuttle plasmid (Torchia and Hopper, 1986, *Genetics* 113: 229–246). Plasmid pT1-3B was digested with the restriction enzyme NheI (New England Biolabs, Beverly, Mass.) according to the manufacturer's instructions, and the resulting 2.7 kb fragment comprising the GAL3 gene was separated by preparative agarose gel electrophoresis and isolated using the GENE CLEAN II system (obtained from BIO 101, Vista, Calif.) according to manufacturer's instructions. Vector pRS414 (ATCC Accession No. 87519, American Type Culture Collection, Manassas, Va.), which carries the TRPI, CEN6, and ARSH4 genes (Sikorski and Hieter, 1989, *Genetics* 122: 19–27) was digested with the restriction enzyme SpeI (New England Biolabs) according to the manufacturer's instructions. The 2.7 kb NheI fragment of pT1-3B, isolated as described above, and the SpeI-digested pRS414 vector were mixed and ligated for 10 h at 16° C. using T4 DNA ligase (New England Biolabs) according to manufacturer's instructions. Following the ligation reaction, the reaction mixture was used to transform bacteria of *E. coli* strain D5α (obtained from Gibco-BRL, Gaithersburg, Md. and Clonetech Labs Inc., Palo Alto, Calif.) and subjected to ampicillin selection using the procedure of Hanahan (1983, *J. Molec. Biol.* 166: 557–580) as detailed in Sambrook et al. (1990, *Molecular Cloning: A Laboratory Manual*, Cold Spring Harbor Laboratory Press, Cold Spring Harbor, N.Y.). At least ten ampicillin-resistant colonies were isolated and plasmid DNA extracted using a Qiagen plasmid preparation kit (Qiagen, Inc., Chatsworth, Calif.) according to manufacturer's instructions. The isolated plasmid DNAs were subjected to restriction enzyme digestion analysis to identify the desired plasmid. The resulting plasmid was termed pTEB8 (ATCC Accession No. 207163), the structure of which is shown in FIG. 2.

EXAMPLE 2

Preparation of Plasmid pPX01 Containing the GAL3 Gene, the GAL80 gene, and the URA3 gene Plasmid pTEB8 was digested with restriction enzymes SacI and BstEII (New England Biolabs) according to the manufacturer's instructions. A 2.4 kb fragment containing the GAL3 gene was isolated and treated for 20 min. at 21° C. with Klenow fragment of *E. coli* DNA polymerase I (obtained from New England Biolabs) according to the manufacturer's instructions to render the ends blunt. Plasmid pMPW12+80 (ATCC Accession No. 207166), which contains the GAL80 gene, the URA3 gene and a GAL4 gene tagged with an epitope (901) insertional mutation at the ClaI site, was digested with SpeI and treated for 20 min. at 21° C. with Klenow fragment according to the manufacturer's instructions, and subsequently treated with shrimp alkaline phosphatase (obtained from Amersham Life Sciences, Cleveland, Ohio) for 45 min. at 37° C. to remove terminal phosphate groups. The blunt-ended 2.4 kb SacI/BstEII fragment of pTEB8 was ligated with the pMPW12+80 fragment using T4 DNA ligase at 21° C. for 4h according to the supplier's instructions. Following this ligation, the reaction mixture was used to transform bacterial cells and grown in the presence of ampicillin as described above. At least ten ampicillin-resistant colonies were isolated and plasmid DNA extracted and characterized by restriction enzyme digestion analysis as described above. The resulting plasmid was termed pPX01 (ATCC Accession No. 207167).

EXAMPLE 3

Preparation of Plasmid pPX02 Containing the GAL3 Gene, the GAL80 Gene, the URA3 Gene and a Wild-Type GAL4 Gene Plasmid pJG34 (ATCC Accession No. 207164), containing the wild-type GAL4 gene, was cut with BamHI and SalI (New England Biolabs) according to the manufacturer's instructions. A 1.7 kb fragment containing the wild-type GAL4 promoter and the GAL4 protein coding region up through amino acid 412 and was separated by preparative agarose gel electrophoresis and isolated using the GENE CLEAN II system (BIO 101) according to manufacturer's instructions. Plasmid pPX01 (described in Example 2 above) was then cut with BamHI and SalI according to the manufacturer's instructions resulting in three fragments: a 9.5 kb BamHI/SalI fragment containing the portion of wild-type GAL4 extending from amino acid 413 to the end, as well as the GAL80, the GAL3 and URA3 genes; a 3.7 kb BamHI fragment containing pBR322 sequences; and a 1.8 kb fragment containing the yeast GAL10 promoter and nucleic acids coding for the first 412 amino acids of the 901 insertion mutant of Gal4, including the insertional 901 mutation at the ClaI site at amino acid 147. The 9.5 kb and 3.7 kb fragments were separated by preparative agarose gel electrophoresis and isolated using the GENE CLEAN II system (BIO 101) according to manufacturer's instructions. The 3.7 kb fragment was treated with shrimp alkaline phosphatase (Amersham Life Sciences) for 45 min at 37° C. according to the manufacturer's instructions to remove terminal phosphates. The 1.7 kb BamHI/SalI fragment from pJG34, the 3.7 kb BamHI fragment from pPX01 and the 9.5 kb BamHI/SalI fragment from pPX01 were mixed at a ratio of 0.2 µg: 0.4 µg:1.0 µg, and ligated using T4 DNA ligase (New England Biolabs) for 13 h at 16° C. according to the manufacturer's instructions. Following this ligation, the reaction mixture was used to transform bacterial cells and grown in the presence of ampicillin as described above. Forty ampicillin-resistant colonies were isolated and plasmid DNA extracted and characterized by restriction enzyme digestion analysis as described above. The resulting plasmid was termed pPX02 (ATCC Accession No. 207165).

EXAMPLE 4

Preparation of Plasmid MEGA2

Plasmid pPX02 was digested with BamHI (New England Biolabs) according to the manufacturer's instructions and the resulting 11 kb fragment containing the entire wild-type GAL4 gene, as well as the GAL80, GAL3 and URA3 genes, was separated by preparative agarose gel electrophoresis and isolated using the GENE CLEAN II system (BIO 101) according to the manufacturer's instructions. Plasmid pC1/1 (obtained from the Dept. of Biochemistry, University of Washington, Seattle, Wash.) containing the entire yeast 2-micron circle, *E. coli* pBR322 plasmid sequences and the defective LEU2 gene variant, leu2-d, was digested with BamHI and treated with shrimp alkaline phosphatase (Amersham Life Sciences) as described above, each procedure performed according to the manufacturer's instructions. The linearized 12 kb pC1/1 fragment was mixed at a 1:1 ratio with the 11 kb fragment from pPX02 and ligated using T4 DNA ligase (New England Biolabs) for 13 h at 16° C. according to the manufacturer's instructions. Following this ligation, the reaction mixture was used to transform bacterial cells and grown in the presence of ampicillin as described above. Sixteen ampicillin-resistant colonies were isolated and plasmid DNA extracted and characterized by restriction enzyme digestion analysis as described above. The resulting plasmid was termed pMEGA2 (ATCC Accession No. 207162).

EXAMPLE 5

Preparation of Plasmid pMEGAMEL-1

The plasmid MEGA2 was digested with NotI (Gibco-BRL) under conditions recommended by the supplier to yield a full length linear form of the plasmid. This fragment was treated with Klenow fragment to create blunt ends. This fragment was then electrophoresed on a 1% agarose gel and the DNA purified using the GENE CLEAN 11 system (BIO101) as described above and under conditions recommended by the supplier. This DNA was then treated with shrimp alkaline phosphatase (Amersham Life Sciences) to remove the terminal phosphate groups as described above.

Following heat inactivation of the phosphatase at 65° C., the fragment was blunt-end ligated to a HindIII and BamHI-digested, Klenow-treated, blunt-ended 4.4 kb DNA fragment bearing the MEL1 gene from plasmid pMP550 (Post-Beittenmiller et al., 1984, *Molec. Cell. Biol.* 4: 1238–1245). Ligation was performed using T4 DNA ligase (New England Biolabs) for 14 h at 16° C. according to manufacturer's instructions. Following this ligation, the reaction mixture was used to transform bacterial cells and the cells were grown in the presence of ampicillin as described above. Twenty-four ampicillin-resistant colonies were isolated and plasmid DNA extracted and characterized by restriction enzyme digestion analysis as described above. The resulting plasmid was termed pMEGAMEL1 (ATCC Accession No. 207161).

EXAMPLE 6

Galactose Induced Expression of a Gal3p/Gal80p/Gal4p Switch Complex Regulated Gene Carried in the NotI Site of Plasmid MEGA2

Plasmids pMEGAMEL-1 and an identical plasmid (pC1/1-URA) that lacked the GAL4, GAL3 and GAL80 genes, were introduced separately into *Saccharomyces cerevisiae* Sc338, a wild type yeast strain cured of the 2 micron plasmid (Erhart & Hollenberg, 1981, Curr. Genet. 3: 83–89.). The transformants were grown at 30° C. to stationary phase in synthetic medium deficient for uracil and containing glycerol-lactic acid as carbon source. An aliquot was diluted into synthetic medium deficient for leucine and containing glycerol-lactic acid as carbon source, and grown at 30° C. to an $A_{600}$=1.0, at which time galactose was added to a final concentration of 2% (w/v). After 2 hours cells were harvested, washed, and lysates prepared for immunoblotting, performed as described in Blank et al. (1997, *Molec. Cell. Biol.* 17: 2566–2575). Lysates were electrophoresed in 6% polyacrylamide gels and the proteins were blotted onto nitrocellulose paper. The α-galactosidase protein encoded by the MEL1 gene was detected on the immunoblot using an antibody prepared against purified α-galactosidase (Sumner-Smith et al., 1985, *Gene* 36: 333–340). The α-galactosidase protein was specifically detected on the blot in extracts prepared from the pMEGAMEL-1 transformed cells of Sc338. α-galactosidase, which was encoded by the single-copy chromosomal MEL1 gene, was also detected in Sc338 cells carrying pC1/1-URA3. At 2 hours after the addition of galactose, the Sc338 cells carrying pMEGAMEL-1 contained 40- to 50fold more α-galactosidase protein than did Sc338 cells carrying pC1/1-URA3. These results demonstrated that the transcription factor cassette encoded in the MEGAMEL-1 plasmid was capable of producing high-level recombinant polypeptide expression in transformed yeast cells.

EXAMPLE 7

Preparation of Plasmid MEGA2ΔURA3

An alternative embodiment of MEGA2 is constructed wherein the URA3 gene is deleted from the plasmid. This plasmid is referred to as MEGA2ΔURA3.

Construction of MEGA2ΔURA3: MEGA2ΔURA3 is constructed using an embodiment of the plasmid pMPW12+80 having had the URA3 gene deleted therefrom. Using this embodiment of pMPW12+80, MEGA2,ΔURA3 is constructed using the same protocol used to produce MEGA2, as disclosed in Examples 1–4 above (see also FIG. 2). Deletion of URA3 from pMPW12+80 is performed as follows. The plasmid is digested NsiI and SpeI (obtained from New England Biolabs), according to the instructions of the supplier. This digestion produces two fragments having sizes of approximately 1750bp and 11,200 bp. These fragments are separated by preparative agarose gel electrophoresis and the larger fragment isolated using the GENE CLEAN II system (BIO 101), according to the manufacturer's instructions. This fragment is then circularized by ligation using T4 DNA ligase (New England Biolabs) for 13 hr at 16° C. in the presence of an adaptor comprised of two annealed synthetic oligonucleotides having the following sequence:

| CTAGTTAGGTAATGATGCA | (SEQ. ID NO. 19) |
|---|---|
| TCATTACCTAA | (SEQ. ID No. 20). |

Annealing these oligonucleotides produces a double stranded DNA adaptor having a 3' overhang (3'-ACGT-5') at one end that hybridizes with the 3' overhang of the NsiI end of the larger fragment, and, at the other end of the adaptor, a 5' overhang (5'-CTAG-3') that hybridizes with the 5' overhang of the SpeI end of the larger fragment. This ligation recreates both the NsiI and SpeI sites in the resulting, circularized plasmid, but the URA3 gene that was originally located between them in pMPW12+80 is deleted. The resulting new pMPW12+80ΔURA3 variant is used to construct MEGA2ΔURA3 by following all of the subsequent steps shown above for the construction of MEGA2.

MEGA2ΔURA3 is useful, inter alia, because a smaller plasmid is generally more stable, particularly in embodiments wherein a nucleic acid encoding a recombinant polypeptide is cloned into a unique restriction enzyme recognition site of the MEGA2 plasmid. In addition, in embodiments of the invention wherein a second construct encoding a recombinant polypeptide is introduced into a yeast cell already comprising MEGA2ΔURA3, the absence of URA3 in MEGA2ΔURA3 permits the use of URA3 as a selectable marker for said second recombinant expression construct.

EXAMPLE 8

Preparation of Plasmid MEGA3

In another alternative embodiment, an epitope tag was introduced into the GAL4 gene of the MEGA2 plasmid, to produce the plasmid MEGA3 (See Kolodziej and Young, 1991, *Methods in Enzymology* 194: 508–519; Field et al., 1988, *Molec. Cell. Biol.* 8: 2159–2165).

Construction of pMEGA3: pMEGA3 is substantially identical to pMEGA2, and has the additional modification that the GALA gene is "epitope tagged" at the ClaI site in GAL4 codon 147. The epitope tag is the "901 epitope" comprising 15 amino acids from the SV40 virus large T antigen. An epitope-tagged version of pMEGA3 was constructed as follows. The plasmid pJG34 (ATCC Accession No. 207164; see FIG. 2) was subjected to partial digestion with ClaI (New England Biolabs). The digested DNA was fractionated by preparative agarose gel electrophoresis and a fragment corresponding to full length pJG34 (10,523 bp) was isolated using GENE CLEAN II system (BIO 101) according to the manufacturer's instructions. The DNA was then treated for 20 min. at 21° C. with Klenow fragment of *E. coli* DNA polymerase I (New England Biolabs) according to the manufacturer's instructions, in order to produce blunt ends. This blunt ended DNA was then self-ligated (recircularized) using T4 DNA ligase (New England Biolabs) according to manufacturer's instructions for 4 hr at 21° C. The products of this ligation reaction mixture were then used to transform bacterial cells and ampicillin-resistant clones selected. Plasmid DNA was extracted and characterized by restriction analysis to identify clones in which the ClaI site at bp #8167 (outside of the GAL4 region) was deleted and the ClaI site at bp #876 (inside GAL4 at codon #147) remained. Once a clone having this pattern of ClaI restriction enzyme recognition sites was identified, the bacterial colony having this clone was amplified and plasmid DNA isolated therefrom. This clone, termed pJG34ΔCla8167, was digested with ClaI, and the digest fractionated by preparative agarose gel electrophoresis. A fragment having a size corresponding to full length pJG34☐Cla8167 was isolated using GENE CLEAN II system (BIO 101) according to the manufacturer's instructions. This isolated fragment was ligated according to the manufacturer's instructions using T4 DNA ligase (New England Biolabs) for 13 hr at 16° C. with a double-stranded DNA fragment produced by annealing oligonucleotides having the following sequence:

CGATTCAGCCATATCACATTTGTAGAG-
GTTTTACTTGCTTTAAAAAAC (SEQ ID No. 21)

and

CGGTTTTTTAAAGCAAGTAAAACCTCTA-
CAAATGTGATATGGCTGAAT (SEQ ID No. 22)

(Cavender et al., 1995, *J. Virol.* 69: 923–934).

These two annealed oligonucleotides encode 15 amino acids comprising the 901 epitope of the SV40 large T antigen, and each end of this fragment comprises an overhang compatible with the ClaI sites at each end of the ClaI-linearized pJG34ΔCla8167 fragment. This plasmid is used in place of pJG3[4] in the plasmid construction scheme described in Examples 1–4 and FIG. 2 above, using the identical synthetic steps. The resulting plasmid, pMEGA3, is identical to pMEGA2, except that the GAL4 gene contains an in-frame insertion of 15 amino acids from SV40 T antigen between amino acid residue 147 and 148. This embodiment of the recombinant expression constructs of the invention is advantageous because a monoclonal antibody specific for the SV40 epitope (anti-901; Cavender et al., 1995, *J. Virol.* 69: 923–934), rather than apolyclonal anti-Gal4 antisera, can be used to monitor the level of Gal4 protein in the yeast cells of the invention.

It should be understood that the foregoing disclosure emphasizes certain specific embodiments of the invention and that all modifications or alternatives equivalent thereto are within the spirit and scope of the invention as set forth in the appended claims.

What is claimed is:

1. A high copy number recombinant expression construct that permits high-level expression of a polypeptide in yeast, said construct comprising:
   a nucleic acid encoding a plurality of trans-acting transcription factors,
   a nucleic acid encoding a yeast selectable marker that provides an inefficiently selected phenotype, and
   a nucleic acid encoding a yeast origin of replication.

2. A recombinant expression construct according to claim 1 wherein the nucleic acid encoding the plurality of trans-acting transcription factors is isolated from a yeast galactose regulon.

3. A recombinant expression construct according to claim 1 wherein the nucleic acid encoding the trans-acting transcription factors comprises a nucleic acid encoding at least one temperature-sensitive transcription factor.

4. A recombinant expression construct according to claim 1 wherein the inefficiently-selected yeast selectable marker is yeast leu2-d gene.

5. A recombinant expression construct according to claim 1 wherein the yeast origin of replication is the 2-micron circle.

6. A recombinant expression construct according to claim 1 further comprising at least one unique restriction site.

7. A recombinant expression construct according to claim 1 further comprising a nucleic acid encoding an efficiently selected yeast selectable marker.

8. A recombinant expression construct according to claim 1 further comprising:
   a nucleic acid encoding a bacterial origin of replication, and
   a nucleic acid encoding a bacterial selectable marker.

9. A method of producing a transformed yeast cell that induces high-level expression of a polypeptide, said method comprising the step of transforming the yeast cell with the recombinant expression construct of claim 1.

10. A transformed yeast cell comprising a recombinant expression construct according to claim 1.

11. A transformed yeast cell comprising a first recombinant expression construct according to claim 1 and a second high copy number recombinant expression construct comprising a nucleic acid encoding a polypeptide operatively linked to a regulatable promoter, wherein the regulatable promoter is regulated by the trans-acting transcription factors encoded by the first recombinant expression construct.

12. A recombinant expression construct according to claim 1 further comprising:
   an inducible cis-acting control element,
   a regulatable promoter, operatively linked to and regulated by said inducible cis-acting control element, and
   a nucleic acid encoding a polypeptide to be expressed, operatively linked to said regulatable promoter.

13. A recombinant expression construct according to claim 2 wherein the trans-acting transcription factors are a GAL3 gene, a GAL4 gene and a GAL80 gene.

14. A recombinant expression construct according to claim 5 wherein the unique restriction site is a NotI, AatII, SacII or PmeI site.

15. A recombinant expression construct according to claim 7 wherein the efficiently selected yeast selectable marker is URA3.

16. A recombinant expression construct according to claim 14 wherein the bacterial selectable marker encoding nucleic acid encodes an ampicillin resistance, tetracycline resistance, neomycin resistance or chloramphenicol resistance gene.

17. A recombinant expression construct according to claim 14 wherein the bacterial origin of replication and the bacterial selectable marker are each derived from plasmid pBR322.

18. A transformed yeast cell according to claim 15 wherein the yeast cell is of a genera selected from the group consisting of the genera Saccharomyces, Kluyveromyces and Pichia.

19. A method of producing a transformed yeast cell that permits high-level expression of a polypeptide, said method comprising the step of transforming the yeast cell of claim 10 with a second high copy number recombinant expression construct comprising a nucleic acid encoding the polypeptide that is operatively linked to a transcription control sequence responsive to the trans-acting factors encoded by the first recombinant expression construct.

20. A yeast cell according to claim 11 wherein the second high copy number recombinant expression construct comprises:
   an inducible cis-acting control element, and
   a regulatable promoter, operably linked to and regulated by said inducible cis-acting control element, wherein the regulatable promoter is regulated by the trans-acting transcription factors encoded by the first recombinant expression construct.

21. A method of producing a transformed yeast cell that induces high-level expression of a polypeptide, said method comprising the step of transforming the yeast cell with the recombinant expression construct of claim 12.

22. A transformed yeast cell comprising the recombinant expression construct of claim 16.

23. A transformed yeast cell according to claim 19 wherein the yeast cell is selected from the group consisting of: *S. cerevisiae, S. carlsbergensis, S. diastaticus, S. oviformis, S. norbensis, S. rouxii, Kluyveromyces lactis* and *Pichia pastoris*.

24. A yeast cell according to claim 20 wherein the trans-acting transcription factor encoding nucleic acid encodes a Gal3 protein, a Gal4 protein and a Gal80 protein, and wherein the regulatable promoter operatively-linked to the inducible cis-acting control element is induced by galactose.

25. A yeast cell according to claim 20 wherein the inducible cis-acting control element comprises a UASgal site.

26. A transformed yeast cell according to claim 25 wherein the yeast cell is of a genera selected from the group consisting of the genera Saccharomyces, Kluyveromyces and Pichia.

27. A yeast cell according to claim 22, wherein the trans-acting transcription factor encoding nucleic acid encodes a Gal3 protein, a Gal4 protein and a Gal80 protein, and wherein the regulatable promoter operatively-linked to the inducible cis-acting control element is induced by galactose.

28. A yeast cell according to claim 22, wherein the trans-acting transcription factor encoding nucleic acid encodes a Gal4 protein, a Gal3 protein and a temperature sensitive Gal80 protein, and wherein the regulatable promoter operatively-linked to the inducible cis-acting control element is induced by a temperature change from a temperature permissive for repression to a temperature non-permissive for repression.

29. A yeast cell according to claim 24 wherein the regulatable promoter further comprising: is a GAL1 gene, a GAL7 gene or a GAL10 gene promoter.

30. A method for sustained high-level production of a polypeptide in the yeast cell of claim 24, said method comprising inducing galactose-regulatable promoters in the yeast cell in the presence of galatose, and producing the polypeptide thereby.

31. A transformed yeast cell according to claim 26 wherein the yeast cell is selected from the gropu consisting of: *S. cerevisiae, S. carlsbergensis, S. diastaticus, S. oviformis, S. norbensis, S. rouxii,* and *Kluyveromyces lactis*, and *Pichia pastoris*.

32. A yeast cell according to claim 27 wherein the inducible cis-acting control element comprises a UASgal site.

33. A yeast cell according to claim 27 wherein the regulatable promoter is a GAL1 gene, a GAL7 gene or a GAL10 gene promoter.

34. A method for sustained high-level production of a polypeptide in the yeast cell of claim 28, said method comprising inducing galactose-regulatable promoters in the yeast cell in the presence of galactose, and producing the polypeptide thereby.

35. A method for sustained high-level production of a polypeptide in the yeast cell of claim 28, said method comprising growing the yeast cell at a temperature non-permissive for repression, and producing the polypeptide thereby.

36. A yeast cell according to claim 29 wherein the trans-acting transcription factor encoding nucleic acid encodes a Gal4 protein, a Gal3 protein and a temperature sensitive Gal80 protein, and wherein the regulatable promoter operatively-linked to the inducible cis-acting control element is induced by a temperature change from a temperature permissive for repression to a temperature non-permissive for repression.

37. A method for sustained high-level production of a polypeptide in the yeast cell of claim 36, said method comprising growing the yeast cell at a temperature non-permissive for repression, and producing the polypeptide thereby.

38. Plasmid pMPW12+80 identified by ATCC Accession Number 207166.

39. Plasmid pTEB8 identified by ATCC Accession Number 207163.

40. Plasmid pJG34 identified by ATCC Accession Number 207164.

41. Plasmid pPX01 identified by ATCC Accession Number 207167.

42. Plasmid pPX02 identified by ATCC Accession Number 207165.

43. A recombinant expression construct that permits high-level expression of polypeptides in yeast, said construct comprising:
   a nucleic acid encoding a plurality of trans-acting transcription factors,
   a nucleic acid encoding a first yeast selectable marker that provides an inefficiently selected phenotype,
   a nucleic acid encoding a yeast origin of replication,
   at least one unique restriction site,
   a nucleic acid encoding a second yeast selectable marker that provides an efficiently selected phenotype,
   a nucleic acid encoding a bacterial origin of replication, and
   a nucleic acid encoding a bacterial selectable marker.

44. A recombinant expression construct according to claim 43 wherein the trans-acting transcription factor encoding nucleic acid comprises a GAL4 gene, a GAL80 gene, and a GAL3 gene; the first yeast selectable marker encoding nucleic acid is a leu2-d allele of the yeast LEU2 gene; the second yeast selectable marker encoding nucleic acid is a URA3 gene; the yeast origin of replication encoding nucleic acid is a 2-micron circle plasmid; the bacterial origin of replication encoding nucleic acid and the bacterial selectable marker encoding nucleic acid are each derived from pBR322 plasmid; and the unique restriction sites are sites recognized by the endonucleases NotI, AatII, SacII or PmeI.

45. The recombinant expression construct of claim 44 that is the MEGA2 plasmid identified by ATCC Accession Number 207162.

46. A method of producing a transformed yeast cell that induces high-level expression of a polypeptide, said method comprising the step of transforming the yeast cell with the recombinant expression construct of claim 44.

47. A transformed yeast cell comprising the recombinant expression construct of claim 44.

48. A transformed yeast cell comprising a first recombinant expression construct according to claim 44 and a second high copy number recombinant expression construct comprising a nucleic acid encoding a polypeptide operatively linked to a regulatable promoter comprising at least one UASgal site.

49. A method of producing a transformed yeast cell characterized by high-level expression of a polypeptide, said method comprising transforming the yeast cell of claim 47 with a high copy number recombinant expression construct comprising a nucleic acid encoding the polypeptide operatively linked to a regulatable promoter comprising at least one UASgal site.

50. A yeast cell according to claim 48 wherein transcription from the regulatable promoter is induced by galactose.

51. A method for high-level production of a polypeptide in the yeast cell of claim 48, said method comprising the step of inducing galactose-regulatable promoters in the yeast cell in the presence of galactose, and producing the polypeptide thereby.

52. A method according to claim 49 wherein transcription from the regulatable promoter is induced by galactose.

53. Plasmid pMEGAMEL1 identified by ATCC Accession Number 207161.

* * * * *